(12) United States Patent
Nagy et al.

(10) Patent No.: US 10,370,400 B2
(45) Date of Patent: Aug. 6, 2019

(54) 4-METHYLUMBELLIFERONE DERIVATIVES FOR TREATMENT FOR IMMUNE MODULATION

(71) Applicant: The Board of Trustees of the Leland Stanford Junior University, Palo Alto, CA (US)

(72) Inventors: Nadine Nagy, Palo Alto, CA (US); Jayakumar Rajadas, Cupertino, CA (US); Paul Bollyky, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 15/870,755

(22) Filed: Jan. 12, 2018

(65) Prior Publication Data
US 2018/0201640 A1    Jul. 19, 2018

Related U.S. Application Data

(60) Provisional application No. 62/446,066, filed on Jan. 13, 2017.

(51) Int. Cl.
*C07H 15/26* (2006.01)
*C07H 17/075* (2006.01)
*A61P 37/02* (2006.01)
*A61P 29/00* (2006.01)
*A61P 17/06* (2006.01)
*A61P 37/08* (2006.01)
*A61P 11/06* (2006.01)
*A61P 19/02* (2006.01)
*A61P 3/10* (2006.01)

(52) U.S. Cl.
CPC .............. *C07H 17/075* (2013.01); *A61P 3/10* (2018.01); *A61P 11/06* (2018.01); *A61P 17/06* (2018.01); *A61P 19/02* (2018.01); *A61P 29/00* (2018.01); *A61P 37/02* (2018.01); *A61P 37/08* (2018.01); *C07H 15/26* (2013.01)

(58) Field of Classification Search
None
See application file for complete search history.

(56) References Cited

U.S. PATENT DOCUMENTS 10,285,976 B2 *   5/2019   Bollyky ................. A61K 31/37

* cited by examiner

*Primary Examiner* — Traviss C McIntosh, III
(74) *Attorney, Agent, or Firm* — Christensen O'Connor Johnson Kindness PLLC

(57) ABSTRACT

This disclosure presents 4-MUG derivatives (e.g., 4-MUG ester prodrugs) that reduce or prevent HA synthesis. In some embodiments, the 4-MUG derivatives of the present disclosure can be used to suppress HA synthesis and curtail inflammation.

22 Claims, 15 Drawing Sheets

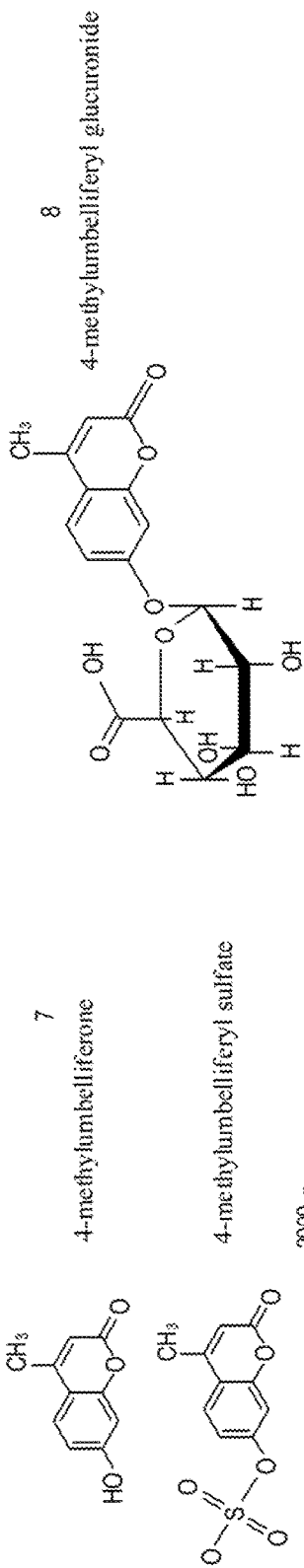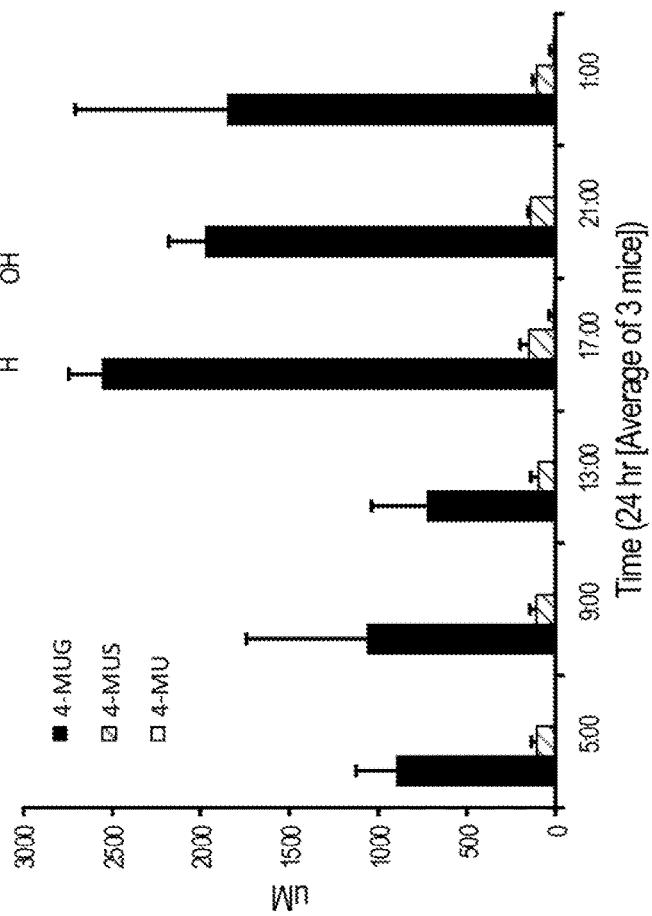
FIG. 1

4-MU derivatives

13 = Ethyl-4-MUG

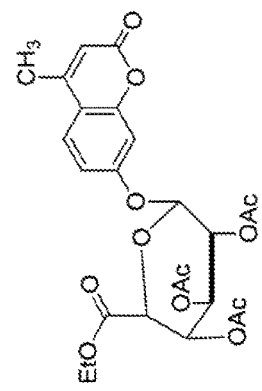

ethyl (2S,3S,4S,5R,6S)-3,4,5-trihydroxy-6-(((4-methyl-2-oxo-2H-chromen-7-yl)oxy)tetrahydro-2H-pyran-2-carboxylate
Chemical Formula: C$_{18}$H$_{20}$O$_9$
Molecular Weight: 380.35

14 = Ethyl-4-MUG-Ac

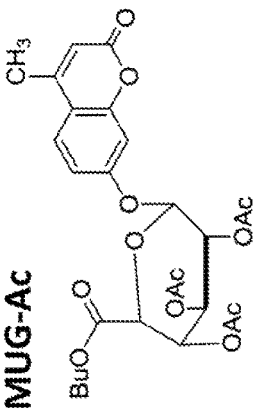

(2S,3S,4S,5R,6S)-2-(ethoxycarbonyl)-6-((4-methyl-2-oxo-2H-chromen-7-yl)oxy)tetrahydro-2H-pyran-3,4,5-triyl triacetate
Chemical Formula: C$_{24}$H$_{26}$O$_{12}$
Molecular Weight: 506.46

15 = Butyl-4-MUG

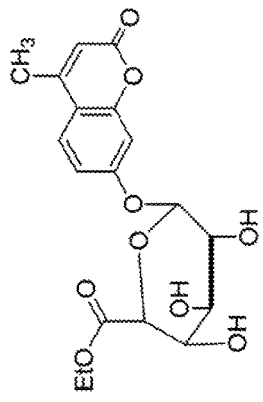

butyl (2S,3S,4S,5R,6S)-3,4,5-trihydroxy-6-((4-methyl-2-oxo-2H-chromen-7-yl)oxy)tetrahydro-2H-pyran-2-carboxylate
Chemical Formula: C$_{20}$H$_{24}$O$_9$
Molecular Weight: 408.40

16 = Butyl-4-MUG-Ac

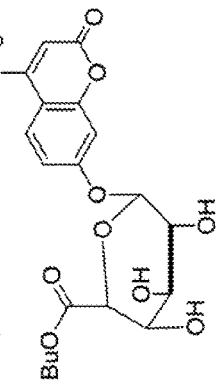

(2S,3S,4S,5R,6S)-2-(butoxycarbonyl)-6-((4-methyl-2-oxo-2H-chromen-7-yl)oxy)tetrahydro-2H-pyran-3,4,5-triyl triacetate
Chemical Formula: C$_{26}$H$_{30}$O$_{12}$
Molecular Weight: 534.51

*FIG. 2*

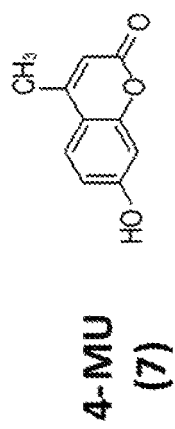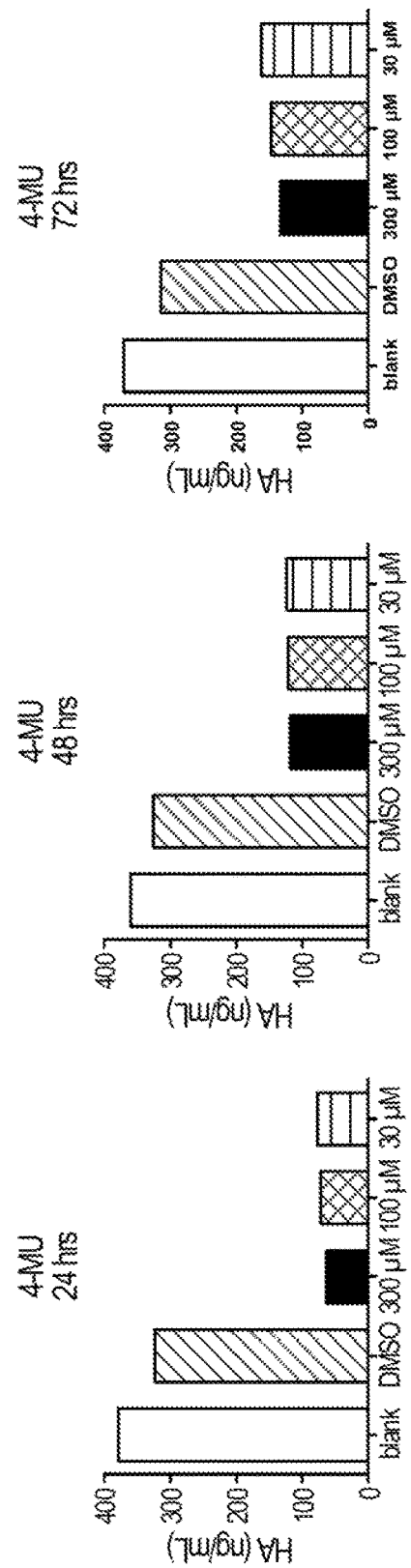
FIG. 3

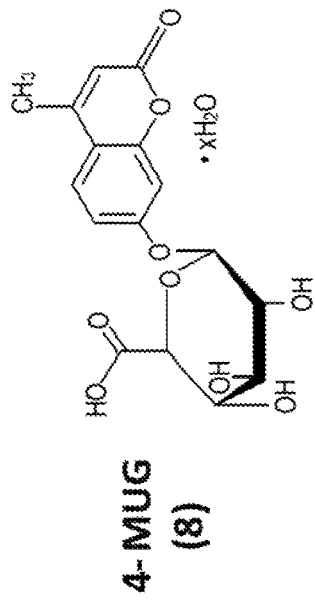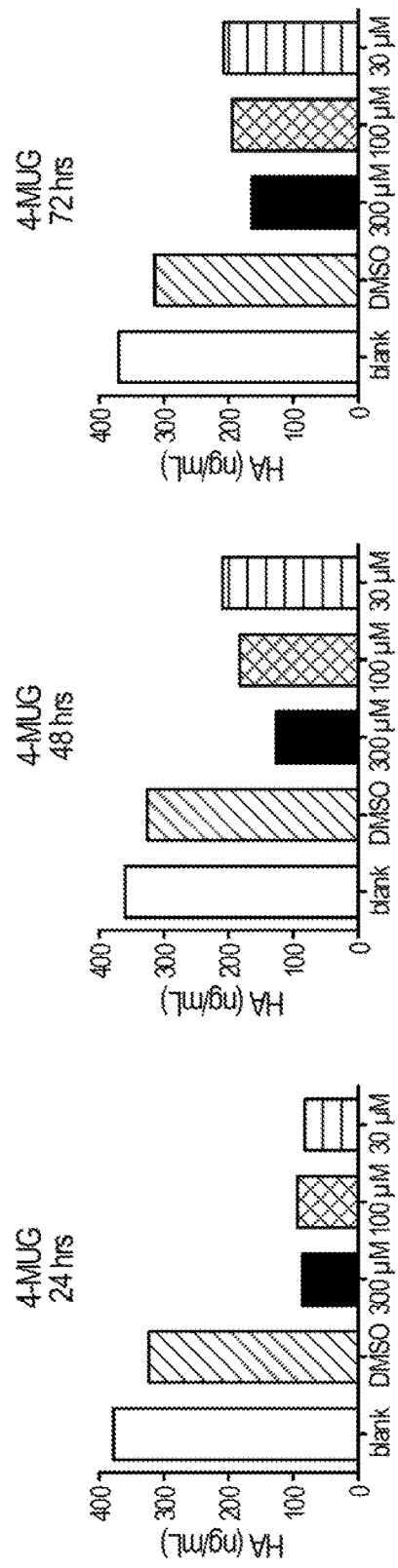
FIG. 4

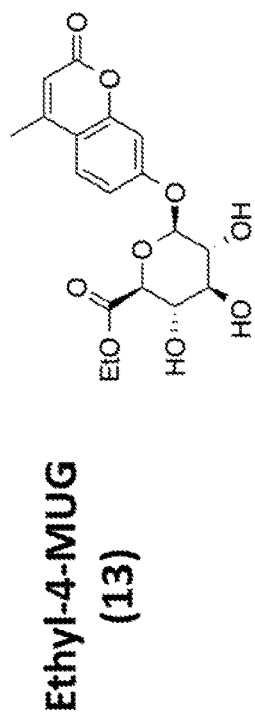
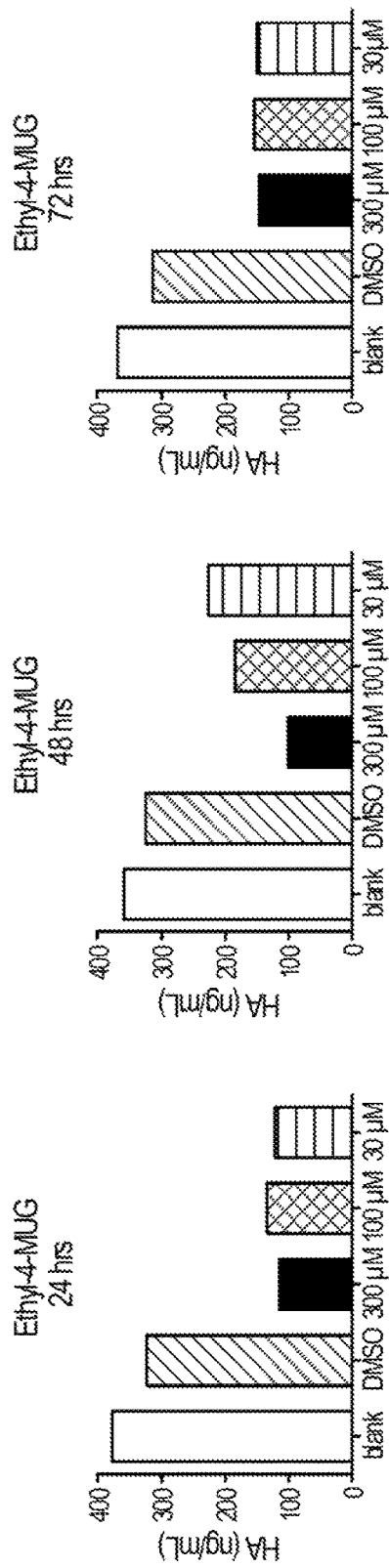
FIG. 5

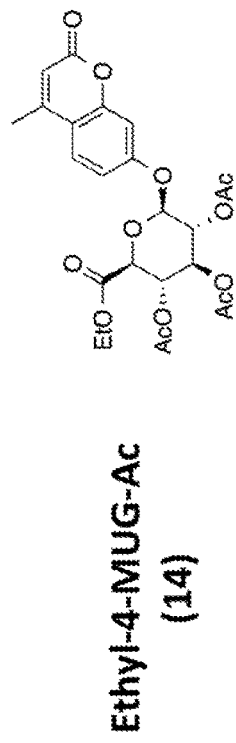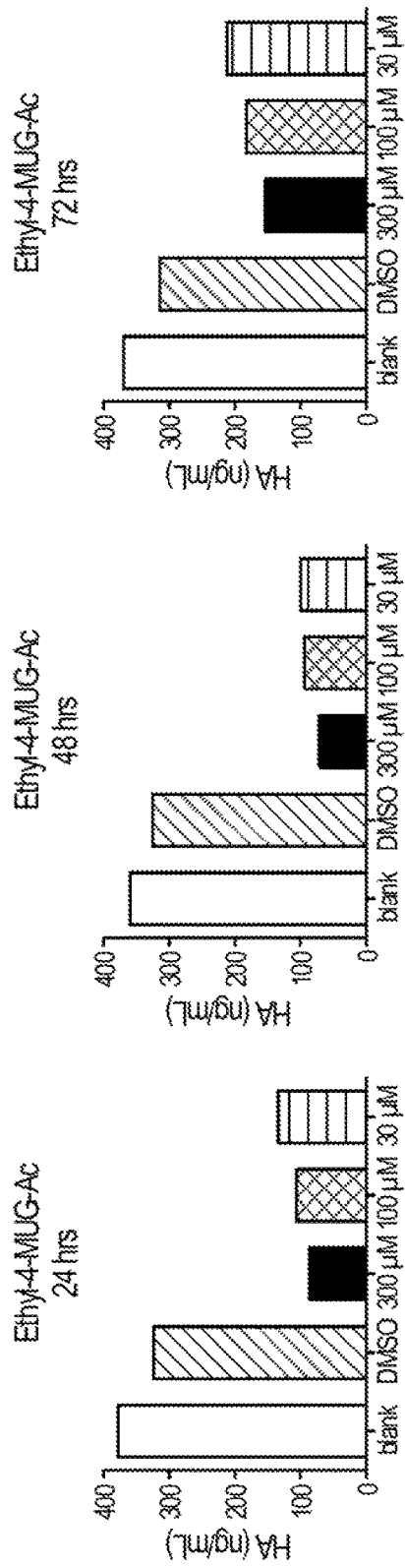
FIG. 6

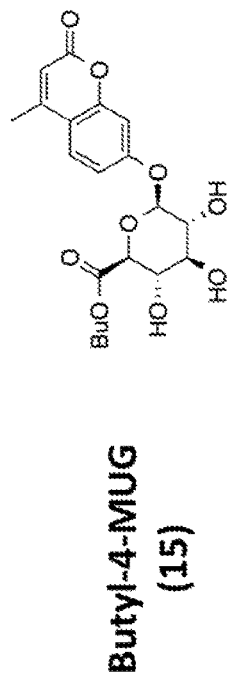
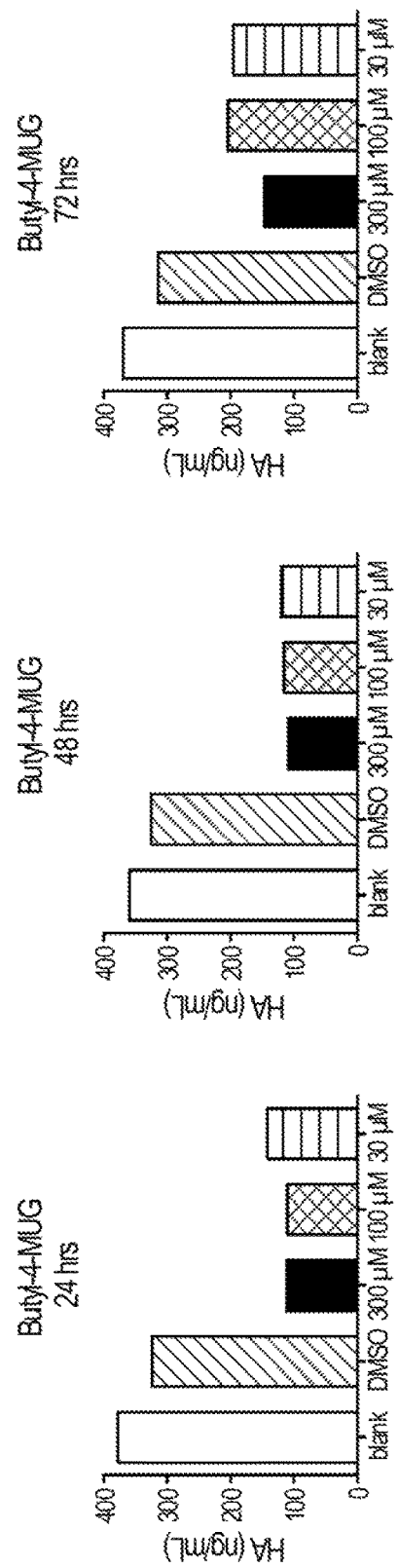
FIG. 7

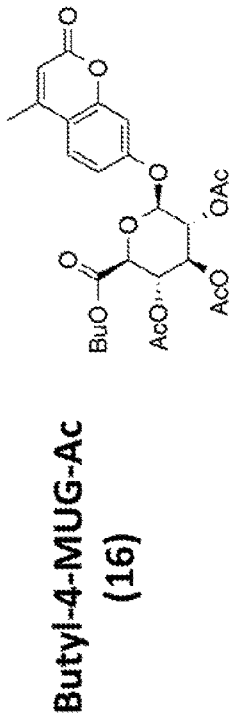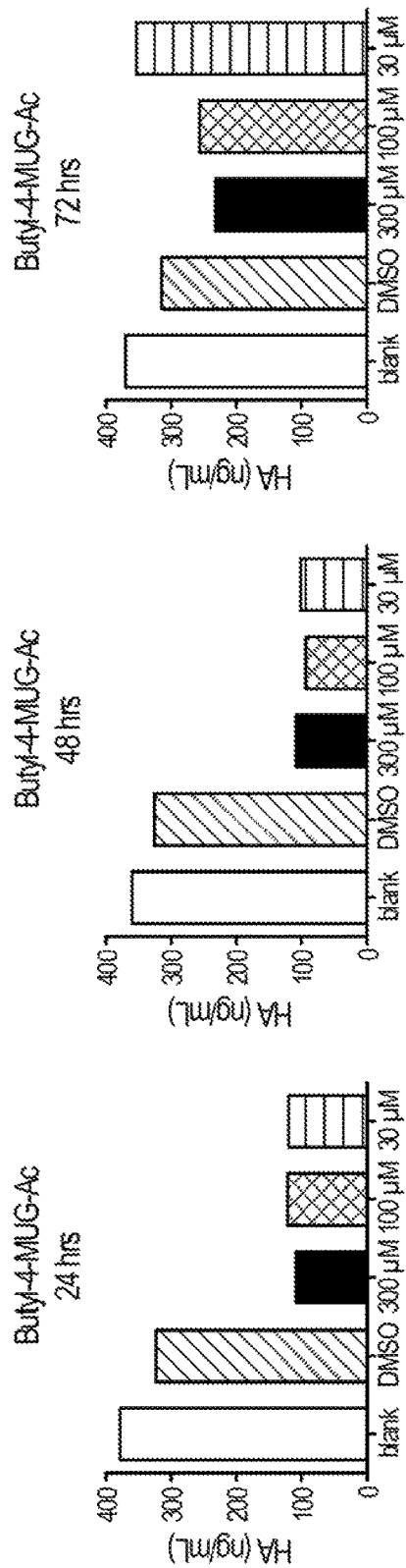
FIG. 8

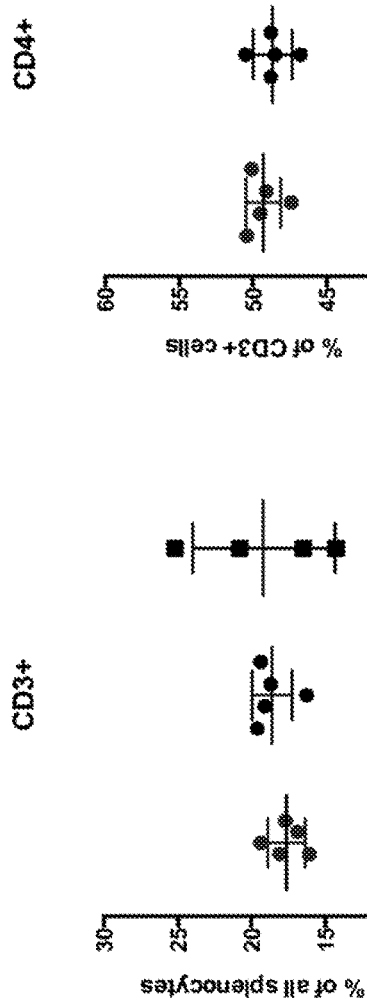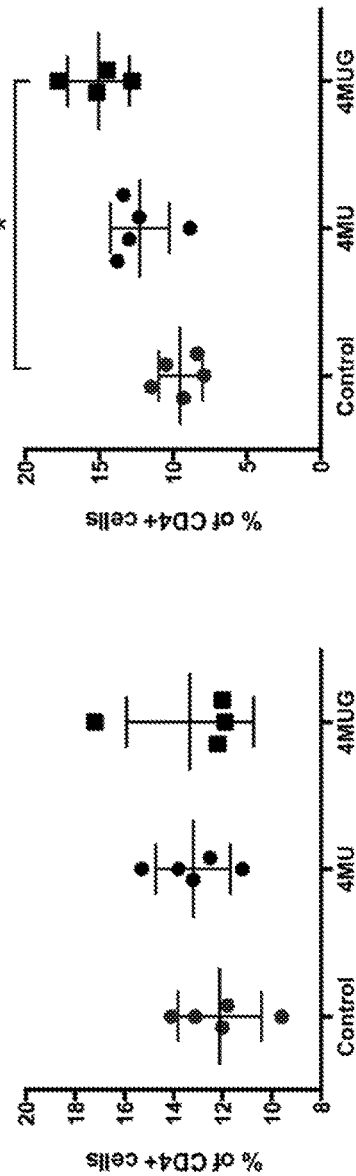
FIG. 11A FIG. 11B FIG. 11C FIG. 11D

4-METHYLUMBELLIFERONE DERIVATIVES FOR TREATMENT FOR IMMUNE MODULATION

CROSS-REFERENCE TO RELATED APPLICATION

This application claims the benefit of U.S. Provisional Application No. 62/446,066, filed Jan. 13, 2017, the disclosure of which is incorporated herein by reference in its entirety.

STATEMENT OF GOVERNMENT LICENSE RIGHTS

This invention was made with Government support under U01 AI101984, R01 DK096087-01 awarded by the National Institute of Health (NIH). The Government has certain rights in the invention.

FIELD OF THE INVENTION

The present disclosure relates to immunomodulatory compositions and methods of using the compositions to inhibit hyaluronan synthesis. The disclosure also relates to compositions and methods for treating an autoimmune disease or inflammatory disorder such as diabetes or multiple sclerosis.

BACKGROUND

Hyaluronan (HA) is an extracellular matrix (ECM) glycosaminoglycan (GAG), which has many roles in normal tissue function and development. This includes providing support and anchorage for cells, facilitating cell-cell signaling, and facilitating cell movement and migration (Jiang D., et al., *Annu. Rev. Cell Dev. Biol.*, 23, 435-461 (2007); Jiang, D., Liang, J. and Noble, P. W., *Physiol. Rev.* 91, 221-264 (2011); Laurent T. C., et al., *Immunol. Cell Biol.* 74, A1-7 (1996)). HA interacts with a complex network of ECM molecules that together exert decisive effects on the physical and immunologic properties of inflamed tissues (Bollyky, P. L., et al., *Curr. Diab. Rep.* 12, 471-480 (2012); Hull, R. L., et al., *J. Histochem. Cytochem.* 60, 749-760 (2012); Bogdani, M. et al., *Diabetes* 63, 2727-2743 (2014); Bogdani, M. et al., *Curr. Diab. Rep.* 14, 552-11 (2014)). In light of its central role in this network, it is believed that HA is a "keystone molecule" in the inflammatory milieu (Bollyky, P. L., et al., *Curr. Diab. Rep.* 12, 471-480 (2012)).

HA is a polymer of disaccharides composed of glucuronic acid and N-acetylglucosamine and linked via alternating β-1, 4 and β-1, 3 glycosidic bonds. HA can be about 25,000 disaccharide repeats in length. In vivo polymers of HA can range in size from 5,000 to 20,000,000 Da. HA is synthesized by a class of integral membrane proteins called HA synthases, of which vertebrates have three types: HAS1, HAS2, and HAS3. These enzymes lengthen HA by repeatedly adding glucuronic acid and N-acetylglucosamine to the nascent polysaccharide as it is extruded through the cell membrane into the extracellular space.

HA synthesis increases substantially at sites of inflammation (Laurent, T. C., et al., Immunol. Cell Biol. 74, A1-7 (1996)), with HA production increasing by as much as 80-fold (Laurent T. C., et al., *Immunol. Cell Biol.* 74, A1-7 (1996)). Increases in HA are associated with many chronic disease processes with unremitting inflammation, including type 2 diabetes (T2D) (Mine, S., et al., *Endocr. J.* 53, 761-766 (2006); Kang, L. et al., *Diabetes* 62, 1888-1896 (2013)), liver cirrhosis, asthma, and other chronic inflammatory diseases of diverse etiologies (Plevris, J. N. et al., *Eur. J. Gastroenterol. Hepatol.* 12, 1121-1127 (2000); Wells, A. F. et al., *Transplantation* 50, 240-243 (1990); Dahl, L. B., et al., *Ann. Rheum. Dis.* 44, 817-822 (1985); Hallgren, R., et al., *Am. Rev. Respir. Dis.* 139, 682-687 (1989); Evanko, S. P., et al., *Am. J. Pathol.* 152, 533-546 (1998); Cheng, G. et al., *Matrix Biol.* 30, 126-134 (2011); Ayars, A. G. et al., *Int. Arch. Allergy Immunol.* 161, 65-73 (2013); Liang, J. et al., *J. Allergy Clin. Immunol.* 128, 403-411.e3 (2011)). HA has been implicated in multiple autoimmune diseases including rheumatoid arthritis (Yoshioka Y, et al., *Arthritis Rheum.* 65, 1160-1170 (2013), lupus (Yung S., et al., *Hindawi* 2012, 207190-9 (2012)), and Hashimotos's thyroiditis (Shan, S. J. C. & Douglas, R. S., *J Neuroophthalmol.* 34, 177-185 (2014)). HA surrounds tumors in diverse forms of cancer (Toole, B. P., *Nat. Rev. Cancer* 4, 528-539 (2004)), this accumulation of HA is part of a larger pattern of ECM deposition associated with persistent inflammation.

HA increases local edema (Waldenström, A., et al., *J. Clin. Invest.* 88, 1622-1628 (1991) and contributes to an inflammatory cascade that drives leukocyte migration, proliferation, differentiation through effects on gene expression and cytokine production and cell survival. These pathways and the impact of HA production on innate immunity are the subject of several excellent reviews (Jiang D., et al., *Annu. Rev. Cell Dev. Biol.*, 23, 435-461 (2007); Jiang, D., Liang, J. and Noble, P. W., *Physiol. Rev.* 91, 221-264 (2011); Petrey, A. C. and la Motte, de, C. A., *Front Immunol.* 5, 101 (2014); Slevin, M. et al., *Matrix Biol.* 26, 58-68 (2007); Sorokin, L., *Nat. Rev. Immunol.* 10, 712-723 (2010)).

Catabolic, low-molecular weight fragments of HA (LMW-HA) act as endogenous danger signals that promote antigenic responses (Termeer, C. et al., *J. Exp. Med.* 195, 99-111 (2002) and immune activation (Jiang, D., Liang, J. and Noble, P. W., *Physiol. Rev.* 91, 221-264 (2011) via CD44 and Toll-like receptor (TLR) signaling (Jiang, D. et al., *Nat. Med.* 11, 1173-1179 (2005); Fieber, C. et al., *J. Cell. Sci.* 117, 359-367 (2004); Termeer, C., et al., *Trends Immunol.* 24, 112-114 (2003); Taylor, K. R. et al., *J. Biol. Chem.* 279, 17079-17084 (2004)). LMW-HA also promotes the activation and maturation of dendritic cells (DC) (Termeer, C. et al., *J. Exp. Med.* 195, 99-111 (2002)), drives the release of pro-inflammatory cytokines such as IL-1β, TNF-alpha, IL-6 and IL-12 by multiple cell types (Bollyky, P. L. et al., *J. Immunol.* 179, 744-747 (2007); Bollyky, P. L. et al., *Proc. Natl. Acad. Sci. U.S.A.* 108, 7938-7943 (2011)), drives chemokine expression and cell trafficking (McKee, C. M. et al., *J. Clin. Invest.* 98, 2403-2413 (1996)), and promotes proliferation (Scheibner, K. A. et al., *J. Immunol.* 177, 1272-1281 (2006)).

Autoimmune Diseases

An autoimmune disease or disorder occurs when the body's immune system attacks and destroys healthy body tissue by mistake. Autoimmune diseases can attack almost any tissue in the body and all autoimmune diseases are characterized by local inflammation and infiltration by immune cells called lymphocytes.

As an example, autoimmune diabetes, also known as type 1 diabetes (T1D) or insulin-dependent diabetes mellitus (IDDM), occurs when the body's immune system mistakenly destroys the pancreatic cells, called beta cells, which make insulin. Damage to beta cells results in an absence or insufficient production of insulin produced by the body. In all autoimmune diseases, including autoimmune diabetes, lymphocytes migrate from the blood stream into target tissues via interactions with the extracellular matrix. In the case of autoimmune diabetes, lymphocytes attack pancreatic islets via interaction with extracellular matrix that lies between islet capillaries and endocrine cells.

One in three hundred American children will develop autoimmune diabetes. Many of these individuals can be identified before they present with hyperglycemia through screening for autoimmune diabetes associated autoantibodies. Thus, there is a therapeutic window where autoimmune diabetes could be prevented, given the knowledge and means to do so. The present disclosure describes novel strategies to reverse, ameliorate, and/or prevent the progression to autoimmune diabetes in at-risk individuals.

As an example, multiple sclerosis (MS) is also an autoimmune disease but in MS the autoimmune activity is directed against central nervous system (CNS) antigens. The disease is characterized by inflammation in parts of the CNS, leading to the loss of the myelin sheathing around neuronal axons (demyelination), axonal loss, and the eventual death of neurons, oligodendrocytes and glial cells. For a comprehensive review of MS and current therapies, see, e.g., Compston, A., et al., *McAlpine's Multiple Sclerosis* 4th ed., Churchill Livingstone Elsevier (2006).

MS is one of the most common diseases of the CNS in young adults, and an estimated 2.5 million people suffer from MS. MS is a chronic, progressing, disabling disease, which generally strikes its victims sometime after adolescence, with diagnosis generally made between 20 and 40 years of age, although onset can occur earlier. The disease is not directly hereditary, although genetic susceptibility plays a part in its development. MS is a complex disease with heterogeneous clinical, pathological and immunological phenotype.

There are four major clinical types of MS: 1) relapsing-remitting MS (RRMS), characterized by clearly defined relapses with full recovery or with sequelae and residual deficit upon recovery; periods between disease relapses are characterized by a lack of disease progression; 2) secondary progressive MS (SPMS), characterized by an initial relapsing remitting course followed by progression with or without occasional relapses, minor remissions, and plateaus; 3) primary progressive MS (PPMS), characterized by disease progression from onset with occasional plateaus and temporary minor improvements allowed; and 4) progressive relapsing MS (PRMS), characterized by progressive disease onset, with clear acute relapses, with or without full recovery; periods between relapses characterized by continuing progression.

Clinically, the illness most often presents as a relapsing-remitting disease and, to a lesser extent, as steady progression of neurological disability. Relapsing-remitting MS presents in the form of recurrent attacks of focal or multifocal neurologic dysfunction. Attacks can occur, remit, and recur, seemingly randomly over many years. Remission is often incomplete and as one attack follows another, a stepwise downward progression ensues with increasing permanent neurological deficit. The usual course of RRMS is characterized by repeated relapses associated, for the majority of patients, with the eventual onset of disease progression. The subsequent course of the disease is unpredictable, although most patients with a relapsing-remitting disease will eventually develop secondary progressive disease. In the relapsing-remitting phase, relapses alternate with periods of clinical inactivity and may or may not be marked by sequelae depending on the presence of neurological deficits between episodes. Periods between relapses during the relapsing-remitting phase are clinically stable. On the other hand, patients with progressive MS exhibit a steady increase in deficits as defined above and either from onset or after a period of episodes, but this designation does not preclude the further occurrence of new relapses.

In healthy individuals (i.e., those without an autoimmune disease or disorder), immune tolerance is maintained by populations of regulatory T-cells including FoxP3+ regulatory T-cells (Treg) (Sakaguchi, S., et al., *Nat. Rev. Immunol.* 10, 490-500 (2010)). Treg absence or depletion leads to multi-systemic autoimmunity, including autoimmune diabetes, in mice and humans (Wildin, R. S., et al., *Nat. Genet.* 27, 18-20 (2001)) whereas adoptive transfer of Treg can abrogate autoimmunity. In MS, Treg present in the CNS are known to limit the extent of neuroinflammation and to facilitate clinical recovery during the mouse model of multiple sclerosis, experimental autoimmune encephalomyelitis (EAE), such that multiple investigative therapeutic strategies to treat autoimmune demyelination are directed at promoting the number and/or function of Treg.

There is a need for developing tools to induce Foxp3+ Treg because of their ability to suppress inflammation, including autoimmunity (Sakaguchi, S., et al., *Nat. Rev. Immunol.* 10, 490-500 (2010)) but also other inflammatory diseases, including T2D (Eller, K. et al., *Diabetes* 60, 2954-2962 (2011)). However, existing therapies have not managed to induce stable, functional FoxP3+ Treg. This is in part because Treg in vivo are a population in flux. Natural Treg (nTreg) continually emerge through thymic selection, whereas induced Treg (iTreg) originate in peripheral tissues in response to inflammatory stimuli and can revert into effector T-cells. This variability in the number and function of local Treg at sites of inflammation can impact the durability of immune tolerance in peripheral tissues.

Despite the fact that the inflammatory milieu is known to have decisive effects on immune tolerance, little is known about how the tissue micro-environment influences the function and number of Treg. Therefore, there is increasing interest in the role of ECM at the interface between lymphocytes and local cells in autoimmunity (Bollyky, P. L., et al., *Curr. Diab. Rep.* 12, 471-480 (2012); Hull, R. L., et al., *J. Histochem. Cytochem.* 60, 749-760 (2012); Irving-Rodgers, H. F. et al., *Diabetologia* 51, 1680-1688 (2008); Ziolkowski, A. F., et al., *J. Clin. Invest.* 122, 132-141 (2012)).

HA in Autoimmune and Inflammatory Diseases.

HA is produced by a variety of cell types in response to inflammatory stimuli including hyperglycemia (Shakya, S., et al., *Int. J. Cell Biol.* 2015, 701738-11 (2015); Wang, A. and Hascall, V. C., *Autophagy* 5, 864-865 (2009)), inflammatory cytokines (Bollyky, P. L. et al., *Cell. Mol. Immunol.* 7, 211-220 (2010)), and other triggers (Lauer, M. E. et al., *J. Biol. Chem.* 284, 5299-5312 (2009)). The HA present within inflamed tissues functions as an endogenous "danger signal" (Noble, P. W., *Matrix Biol.* 21, 25-29 (2002)) and promotes inflammatory responses (Jiang, D., Liang, J. and Noble, P. W., *Physiol. Rev.* 91, 221-264 (2011); la Motte, de, C. et al., *Am. J. Pathol.* 174, 2254-2264 (2009)).

HA is highly abundant within chronically inflamed tissues including for example MS lesions (Back, S. A. et al., *Nat. Med.* 11, 966-972 (2005)). For example, in one study HA was shown to accumulate in demyelinated lesions in MS and EAE. Immunostaining for proteolipid protein (PLP) of a chronic MS lesion showed complete loss of myelin in the center of the lesions. CD44 staining revealed high levels of CD44 in the lesions, and elevated CD44 expression in GFAP-expressing reactive astrocytes were also found. HA staining showed high levels of HA in demyelinated regions of the lesions but at lower levels in the lesion borders (Back, S. A. et al., *Nat. Med.* 11, 966-972 (2005)).

Typically, HA present within chronically inflamed tissues takes the form of short, highly catabolized fragments (as reviewed in Bollyky, P. L., et al., *Curr. Diab. Rep.* 12, 471-480 (2012)) that are pro-inflammatory agonists of Toll-like receptor signalling (Jiang, D., Liang, J. and Noble, P. W., *Physiol. Rev.* 91, 221-264 (2011); Laurent, T. C., et al., *Immunol. Cell Biol.* 74, A1-7 (1996)), driving dendritic cell maturation, and promoting phagocytosis (Termeer, C. et al., *J. Exp. Med.* 195, 99-111 (2002); Jiang, D. et al., *Nat. Med.* 11, 1173-1179 (2005)). HA overexpression tends to drive inflammation (Olsson, M., et al., *PLOS Genetics* 7, e1001332 (2011)) presumably through production of increased HA fragments, while inhibition of HA synthesis, including treatment with 4-methylumbelliferone (4-MU, Hymecromone), tends to reduce inflammation (Yoshioka, Y. et al., *Arthritis Rheum.* 65, 1160-1170 (2013); McKallip, R. J., et al., *Inflammation* 38, 1250-1259 (2015); Colombaro, V. et al., *Nephrol. Dial. Transplant.* 28, 2484-2493 (2013)). With respect to the role of HA in local immune modulation, it is known that low molecular weight HA fragments inhibit the function of FoxP3+ Treg (Bollyky, P. L. et al., *J. Immunol.* 179, 744-747 (2007); Bollyky, P. L. et al., *J. Immunol.* 183, 2232-2241 (2009)). These effects are mediated via TLR signaling and via interactions with the HA receptor CD44.

In the healthy CNS, astrocytes are the main producers of low levels of HA, depositing it as ECM complexes in the spaces between myelinated axons and between myelin sheaths and astrocyte processes (Asher, R., et al., *J. Neurosci. Res.* 28, 410-421 (1991)). Upon injury, however, reactive astrocytes produce abundant amounts of HA, which accumulate in damaged areas (Back, S. A. et al., *Nat. Med.* 11, 966-972 (2005); Bugiani, M. et al., *Brain* 136, 209-222 (2013)). As such, HA is present at high levels in demyelinating lesions in MS patients and in mice with EAE (Back, S. A. et al., *Nat. Med.* 11, 966-972 (2005)).

Recently, it was shown that HA deposits accumulate within the pancreatic islets of individuals with recent-onset T1D (Bogdani, M. et al., *Diabetes* 63, 2727-2743 (2014)). These deposits were present at sites of insulitis (Bogdani, M. et al., *Diabetes* 63, 2727-2743 (2014)). Similar HA deposits were observed in animal models of T1D (Nagy, N. et al., *J. Clin. Invest.* 125, 10.1172/JCI79271-0 (2015)).

Many other chronic inflammatory diseases are also associated with HA deposition. For example, the pathogenesis of T2D is known to have an inflammatory component with inflammation localized to the muscle and adipose tissue (Wellen, K. E. and Hotamisligil, G. S., *J. Clin. Invest.* 115, 1111-1119 (2005)). In T2D HA deposition has been noted in skeletal muscle (Kang, L. et al., *Diabetes* 62, 1888-1896 (2013)), adipose tissue (Liu, L. F. et al., *Diabetologia* 58, 1579-1586 (2015)), and other tissues of obese and diabetic animals (Mine, S., et al., *Endocr. J.* 53, 761-766 (2006); Bowling, F. L., et al., *Nat Rev Endocrinol.* 11, 606-616 (2015); Dalferes, E. R., et al., *Proc. Soc. Exp. Biol. Med.* 148, 918-924 (1975); Dwyer, T. M. et al., *Kidney Int.* 58, 721-729 (2000); Zhu, Y., et al., *Sci. Transl. Med* 8, 323ps4-323ps4 (2016)). As another example many cancers are also associated with abundant HA in the matrix surrounding tumors (Li, Y. and Heldin, P., *Br. J. Cancer* 85, 600-607 (2001); Schwertfeger, K. L., et al., *Front. Immunol.* 6, 236 (2015)).

HA Synthesis Inhibitors

4-MU is a selective inhibitor of HA synthesis. The compound was first used in vitro in 1990 by Nakamura et al., to inhibit HA-synthesis in skin fibroblasts (Nakamura, T. et al., *Biochem. Biophys. Res. Commun.* 172, 70-76 (1990)). In 2004, the mechanism of 4-MU was discovered by Kakizaki et al., and since then it has been used in in vivo studies in mice and rats to investigate the 4-MU influence, mainly in cancer studies (Kakizaki, I. et al., *J. Biol. Chem.* 279, 33281-33289 (2004)); see also, e.g., Yoshihara, S. et al., *FEBS Lett.* 579, 2722-2726 (2005); Lokeshwar, V. B. et al., *Cancer Res.* 70, 2613-2623 (2010) and in atherosclerosis studies (Nagy, N. et al., *Circulation* 122, 2313-2322 (2010)). 4-MU is also already used in humans. It is available without a prescription as Heparvit, a nutraceutical product for cancer patients. Furthermore, it is available with prescription in Europe and Asia to treat biliary spasm under the name Hymecromone. In that setting, the drug has an excellent safety profile and has been used for several years.

One strategy to decrease or prevent the pro-inflammatory activity of LMW-HA within autoimmune lesions is to limit HA synthesis using 4-MU. 4-MU is a derivate that belongs to the coumarin family. Other coumarin derivatives, such as phenprocoumon (Marcumar®) and warfarin (Coumadin®), are used in preventive medicine to reduce cardiovascular events due to their anticoagulatory mechanism. 4-MU is thought to inhibit HA production in at least two ways. First, 4-MU is thought to function as a competitive substrate for UDP-glucuronyltransferase (UGT), an enzyme involved in HA synthesis (Kakiazaki, I., et al., *J. Biol. Chem.* 279, 33281-33289 (2004)). HA is produced by the HA synthases HAS1, HAS2 and HAS3 from the precursors UDP-glucuronic acid (UDP-GlcUA) and UDP-N-acetyl-glucosamine (UDP-GlcNAc). These are generated by the transfer of an UDP-residue to N-acetylglucosamine and glucuronic acid via the UDP-glucuryltransferase (UGT). The availability of UDP-GlcUA and UDP-GlcNAc thereby control HA synthesis (Vigetti, D. et al., *J. Biol. Chem.* 281, 8254-8263 (2006)). In the presence of 4-MU, it covalently binds through its hydroxyl group at position 4 to glucuronic acid via the UGT. As a consequence, the concentration of UDP-glucuronic acid declines in the cytosol and HA synthesis is reduced. This therewith reduces 4-MU the UDP-GlcUA content inside the cells. 4-MU inhibits HA synthesis by depleting the HAS enzyme UDP-GlcUA, which is consumed by 4-MU glucuronidation. So far it is unclear how exactly the second mechanism works, but, 4-MU reduces expression of HAS mRNA expression (Kultti A., et al., *Exp. Cell Res.* 315, 1914-1923 (2009) as well as mRNA for UDP glucose pyrophosphorylase and dehydrogenase (Vigetti, D. et al., *Glycobiology* 19, 537-546 (2009)).

A few studies have investigated the impact of 4-MU on HA synthesis in autoimmunity and inflammation. 4-MU has been used to inhibit HA production by several human pathogens and their interactions with human cells in vitro (Jong, A. et al., *Eukaryotic Cell* 6, 1486-1496 (2007); Kakizaki, I. et al., *Eur. J. Biochem.* 269, 5066-5075 (2002)). In vivo studies showed that 4-MU treatment decreased or prevented lung injury and reduced inflammatory cytokine levels in mouse models of staphylococcal enterotoxin-mediated (McKallip, R. J., et al., *Toxins (Basel)* 5, 1814-1826 (2013)) and lipopolysaccharide-mediated acute lung injury (McKallip, R. J., et al., *Inflammation* 38, 1250-1259 (2015)). 4-MU has also been shown to have protective effects on non-infectious inflammation, including renal ischemia and reperfusion (Colombaro, V. et al., *Nephrol. Dial. Transplant.* 28, 2484-2493 (2013)), and airway inflammation secondary to cigarette smoke, 4-MU also restores normoglycemia and promotes insulin sensitivity in obese, diabetic mice via increased production of adiponectin (Sim, M.-O., et al., Chem. Biol. Interact. 216, 9-16 (2014)). 4-MU has also been reported to ameliorate disease in a limited number of mouse models of autoimmune disease. Specifically, 4-MU treatment was beneficial in the collagen-induced arthritis model where it improved disease scores and reduced expression of matrix metaloproteases (MMPs) (Yoshioka Y, et al., *Arthritis Rheum.* 65, 1160-1170 (2013)). More recently, 4-MU treatment was demonstrated to prevent and treat disease in the experimental autoimmune encephalomyelitis (EAE) model where it increased populations of regulatory T-cells and polarized T-cell differentiation away from pathogenic, T-helper 1 T-cell subsets and towards non-pathogenic T-helper 2 subsets (Mueller, A. M., et al., *J. Biol. Chem.* 289, 22888-22899 (2014)). In addition, 4-MU treatment reduced the number of tumor satellites, inhibited angiogenesis and cell growth in tumors (Yoshihara, S. et al., *FEBS Lett.* 579, 2722-2726 (2005); Lokeshwar, V. B. et al., *Cancer Res.* 70, 2613-2623 (2010); Garcia-Vilas, J. A., et al., *J. Agric. Food Chem.* 61, 4063-4071 (2013)). The existing in vitro and in vivo data suggest that hymecromone can have utility as a component of therapeutic regimens directed against HA-producing cancers.

4-MU treatment has been reported to reduce or prevent cell-cell interactions required for antigen presentation (Bollyky, P. L. et al., *Cell. Mol. Immunol.* 7, 211-220 (2010)) and has been described to have inhibitory effects on T-cell proliferation (Mahaffey, C. L. and Mummert, M. E., *J. Immunol.* 179, 8191-8199 (2007); Mummert, M. E. et al., *J. Immunol.* 169, 4322-4331 (2002)). These effects are consistent with established roles for HA and its receptors in T-cell proliferation, activation, and differentiation (Jiang, D., Liang, J. and Noble, P. W., *Physiol. Rev.* 91, 221-264 (2011); Guan, H., et al., *J. Immunol.* 183, 172-180 (2009); Ponta, H., et al., *Nat. Rev. Mol. Cell Biol.* 4, 33-45 (2003)). There are also indications that 4-MU treatment can make some models of inflammation worse. 4-MU treatment was associated with worse atherosclerosis in ApoE-deficient mice fed a high-fat diet (Nagy, N. et al., *Circulation* 122, 2313-2322 (2010)).

4-MU treatment has been reported to limit the progression of EAE (Mueller, A. M., et al., *J. Biol. Chem.* 289, 22888-22899 (2014); Kuipers, H. F. et al., *Proc. Natl. Acad. Sci. U.S.A.* 113, 1339-1344 (2016)) and autoimmune diabetes in both the DORmO and NOD mouse models (Nagy, N. et al., *J. Clin. Invest.* 125, 10.1172/JCI79271-0 (2015); Kuipers, H. F. et al., *Clin. Exp. Immunol.* 185, 372-381 (2016)). This therapeutic effect was not only a result of the polarization of the T-cell response away from a pathogenic Th1 response, but also the reduction of infiltration of these cells into sites of autoimmune attack. Additionally, because 4-MU treatment lifts the inhibition of FoxP3+ Treg induction and function by LMW-HA, this inhibition of the pathogenic response is aided by an increase of Treg numbers (Nagy, N. et al., *J. Clin. Invest.* 125, 10.1172/JCI79271-0 (2015); Kuipers, H. F. et al., *Proc. Natl. Acad. Sci. U.S.A.* 113, 1339-1344 (2016); Kuipers, H. F. et al., *Clin. Exp. Immunol.* 185, 372-381 (2016)). Furthermore, in addition to sustaining a pro-inflammatory environment in MS lesions, HA deposits have been show to inhibit the maturation of oligodendrocytes, the myelin forming cells of the CNS, in MS and other myelin degenerative disorders, and as such are thought to prevent repair of myelin, further contributing to MS pathogenesis (Back, S. A. et al., *Nat. Med.* 11, 966-972 (2005); Bugiani, M. et al., *Brain* 136, 209-222 (2013)). 4-MU treatment can restore the HA load in inflamed tissues to a dominance of anti-inflammatory high molecular weight (HMW) polymers.

Since more and more studies highlight the role of HA in inflammation, autoimmunity, and cancer, there has been great interest in identifying pharmacologic tools to inhibit HA synthesis. 4-MU has been shown to inhibit HA production in multiple cell lines and tissue types both in vitro and in vivo (Nagy, N. et al., *Circulation* 122, 2313-2322 (2010); Kakiazaki, I., et al., *J. Biol. Chem.* 279, 33281-33289 (2004); Kultti A., et al., *Exp. Cell Res.* 315, 1914-1923 (2009); Bollyky, P. L. et al., *Cell. Mol. Immunol.* 7, 211-220 (2010)), and has received much attention as a potential therapeutic in inflammation, autoimmunity and cancer (Nagy, N. et al., *Front Immunol.* 6, 123 (2015)), unrelated to its clinical use for bile duct disorders (Abate, A. et al., *Drugs Exp. Clin. Res.* 27, 223-231 (2001)). Unfortunately, 4-MU has poor pharmacokinetics and limited bioavailability outside the liver and biliary tract (Nagy, N. et al., *Front Immunol.* 6, 123 (2015); Garrett, E. R., et al., *Biopharm Drug Dispos* 14, 13-39 (1993); Garrett, E. R. and Venitz, J., *J. Pharm. Sci.* 83, 115-116 (1994)).

There is a need for HA synthesis inhibitors that can provide a safe and effective therapy for, for example, autoimmune diseases such as, for example, diabetes and MS and for inflammatory disorders, such as, for example, diabetes and cancer. The present disclosure seeks to fulfill these needs and provides further related advantages.

SUMMARY

In one aspect, the present disclosure features 4-methylumbelliferone glucuronide (4-MUG) derivatives including a compound of Formula (I):

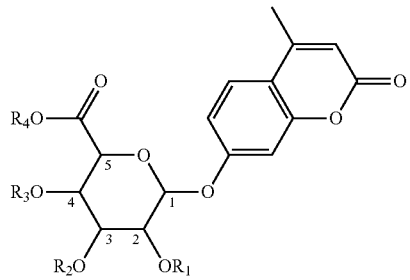

wherein $R_1$ and $R_2$ are each independently selected from H, C(O)—$C_{1-10}$ alkyl, and C(O)—$C_{1-10}$ haloalkyl;

$R_3$ is selected from H, C(O)—$C_{1-10}$ alkyl, C(O)—$C_{1-10}$ haloalkyl, C(O)—$C_{6-10}$ aryl, and C(O)—$C_{5-10}$ heteroaryl, wherein the C(O)—$C_{1-10}$ haloalkyl, C(O)—$C_{6-10}$ aryl, and C(O)—$C_{5-10}$ heteroaryl are each optionally substituted with 1, 2, 3, or 4 substituents independently selected from halo, cyano, and nitro; and $R_4$ is selected from $C_{2-10}$ alkyl and $C_{2-10}$ haloalkyl, or a pharmaceutically acceptable salt thereof.

In another aspect, the present disclosure features a composition including a compound of Formula (I) as described above, or a pharmaceutically acceptable salt thereof, and a pharmaceutically acceptable carrier.

In a further aspect, the present disclosure features a method for intracellular delivery of a 4-methylumbelliferone glucuronide derivative, including contacting a cell with a compound of Formula (I), or a pharmaceutically acceptable salt thereof, as described above.

In a further aspect, the present disclosure features a method of inducing a regulatory T-cell response, including administering to a subject a therapeutically effective amount of a compound of Formula (I), or a pharmaceutically acceptable salt thereof, as described above.

In a further aspect, the present disclosure features a method of inhibiting hyaluronan synthesis in a subject, including administering to the subject a therapeutically effective amount of a compound of Formula (I), or a pharmaceutically acceptable salt thereof, as described above.

In a further aspect, the present disclosure features a method of increasing FoxP3+ regulatory T-cells, including administering to a subject a therapeutically effective amount of a compound of Formula (I), or a pharmaceutically acceptable salt thereof, as described above.

In a further aspect, the present disclosure features a method of treating inflammatory, autoimmune, allergic, or atopic disease in a subject, including administering to the subject a therapeutically effective amount of a compound of Formula (I), or a pharmaceutically acceptable salt thereof, as described above. The inflammatory, autoimmune, allergic, or atopic disease can be selected from the group consisting of diabetes (both type 1 and type 2), pre-diabetes, multiple sclerosis, Sjögrens disease, autoimmune thyroiditis, primary sclerosing cholangitis, rheumatoid arthritis, psoriasis, colitis, lichen planus, psoriasis, eczema, and asthma.

In a further aspect, the present disclosure features a method for treating insulitis and/or reversing progression of diabetes in a subject suffering from or at risk of developing diabetes, the method including administering to the subject a composition including a compound of Formula (I), or a pharmaceutically acceptable salt thereof, in an amount effective to inhibit hyaluronan synthesis in the subject.

In a further aspect, the present disclosure features a method for treating multiple sclerosis in a subject in need thereof, the method including administering to the subject a composition including a compound of Formula (I), or a pharmaceutically acceptable salt thereof, in an amount effective to inhibit hyaluronan synthesis in the subject.

In a further aspect, the present disclosure features a method for treating multiple sclerosis and/or autoimmune demyelination in a subject suffering from or at risk of developing multiple sclerosis, the method including administering to the subject a composition including a compound of Formula (I), or a pharmaceutically acceptable salt thereof, in an amount effective to inhibit hyaluronan synthesis in the subject.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 illustrates the chemical structure of 4-methylunbelliferone (4-MU), 4-methylumbelliferyl sulphate (4-MUS), and 4-methylumbelliferyl glucuronide (4-MUG), and graphically represents a concentration of 4-MU and its metabolites 4-MUG and 4-MUS following administration of 4-MU.

FIG. 2 illustrates the structure and formulae of embodiments of 4-MUG derivatives of the present disclosure.

FIG. 3 illustrates the structure of 4-MU and graphically represents a concentration of HA following exposure to 4-MU.

FIG. 4 illustrates the structure of 4-MUG and graphically represents a concentration of HA following exposure to 4-MUG.

FIG. 5 shows the structure of ethyl-4-MUG and graphically represents a concentration of HA following exposure to ethyl-4-MUG.

FIG. 6 shows the structure of ethyl-4-MUG-Ac and graphically represents a concentration of HA following exposure to ethyl-4-MUG-Ac.

FIG. 7 shows the structure of butyl-4-MUG and graphically represents a concentration of HA following exposure to butyl-4-MUG-Ac.

FIG. 8 shows the structure of butyl-4-MUG-Ac and graphically represents a concentration of HA following exposure to butyl-4-MUG-Ac.

FIG. 11A graphically represent the induction of FoxP3+ regulatory T-cells by 4-MUG. 4-MUG does not increase the numbers of CD3+ T-cells FIG. 11B graphically represent the induction of FoxP3+ regulatory T-cells by 4-MUG. 4-MUG does not increase the numbers of CD4+ T-cells.

FIG. 11C graphically represent the induction of FoxP3+ regulatory T-cells by 4-MUG. 4-MUG does not increase the numbers of CD25+ T-cells.

FIG. 11D graphically represent the induction of FoxP3+ regulatory T-cells by 4-MUG. 4-MUG increases the fraction of Foxp3+ regulatory T-cells. This indicates a specific effect on Foxp3+T regulatory T-cells.

DETAILED DESCRIPTION

Figure 9:
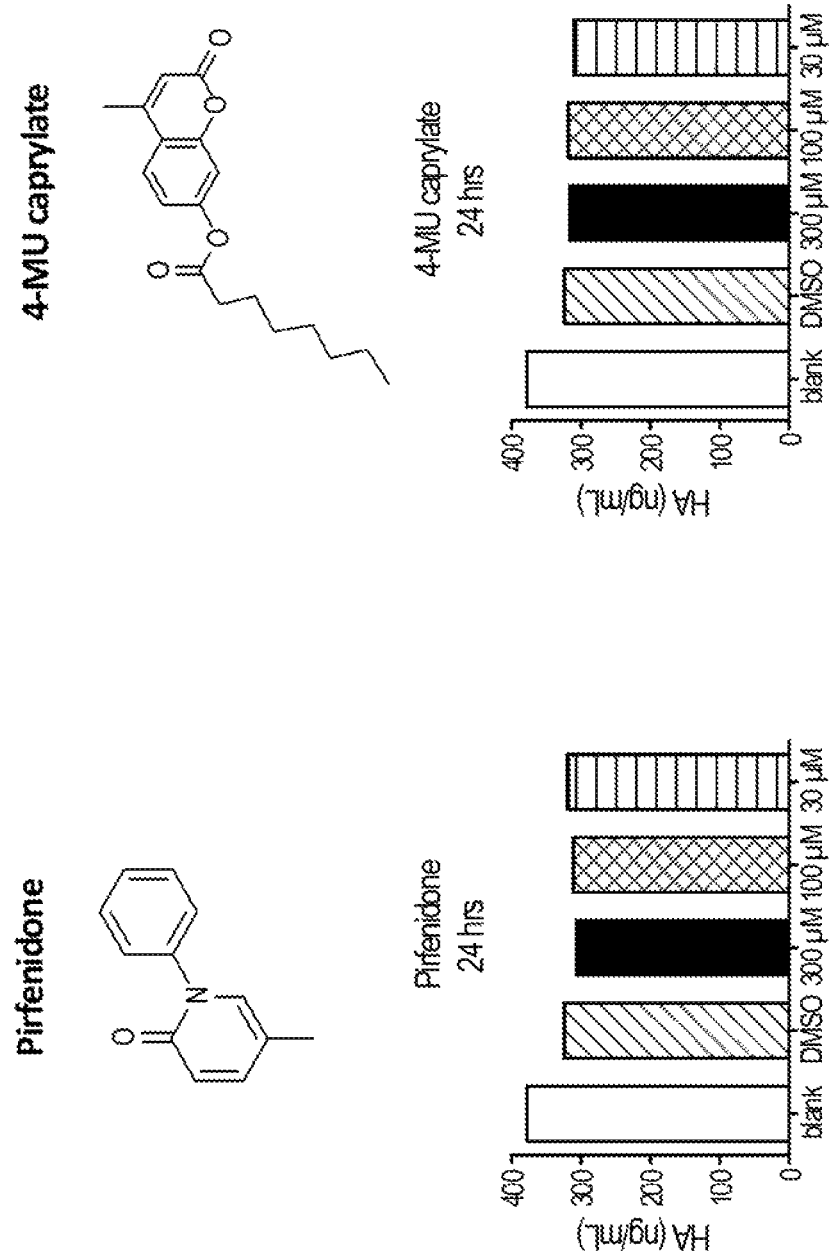
FIG. 9 shows the structure of pirfenidone and 4-MU caprilate and graphically represents a concentration of HA following exposure to pirfenidone and 4-MU caprilate.

Hyaluronan (HA) is an inflammatory mediator that is abundant at sites of chronic diseases of diverse etiologies, including autoimmunity, infection, and cancer. It would be useful to be able to inhibit HA synthesis pharmacologically. One drug that does this is 4-methylumbelliferone. 4-methylumbelliferone glucuronide (4-MUG), a metabolite of 4-MU, is biologically active and inhibits HA synthesis. Previously it was not known that 4-MUG is an inhibitor of HA synthesis. Indeed, the established understanding of the mechanism of action of 4-MU would suggest that it should not be. However, the present disclosure (and the Examples below) show that 4-MUG surprisingly inhibits HA synthesis as effectively as 4-MU. This disclosure presents 4-MUG derivatives (e.g., 4-MUG ester prodrugs) that reduce or prevent HA synthesis. The 4-MUG derivatives of the present disclosure can be used to suppress HA synthesis and curtail inflammation.

Definitions

Unless specifically defined herein, all terms used herein have the same meaning as they would to one skilled in the art of the present disclosure. The following definitions are provided in order to provide clarity with respect to the terms as they are used in the specification and claims to describe the claimed subject matter.

As used herein, the term "regulatory T-cells" or "Treg" cells refers to T-cells which express the cell surface markers CD4+ and CD25+, which express FoxP3 protein as measured by a Western blot and/or FoxP3 mRNA transcript.

As used herein, the term "antigen-specific regulatory T-cells" or "antigen-specific Tregs" refers to Treg cells that were induced in the presence of an antigen and which express the cell surface markers CD4+ and CD25+, which express FoxP3 protein as measured by a Western blot and/or FoxP3 mRNA transcript.

As used herein, the term "derived from" or "a derivative thereof," in the context of peptide or polypeptide sequences, means that the peptide or polypeptide is not limited to the specific sequence described, but also includes variations in that sequence, which can include amino acid additions, deletions, substitutions, or modifications to the extent that the variations in the listed sequence retain the ability to modulate an immune response. In the context of small molecules (i.e., an organic compound having a molecular weight of less than about 1000 Da that can help regulate biological process, with a size on the order of 1 nm), a derivative is a small molecule that has been modified by chemical reaction, such as by acylation, alkylation, halogenation, nitration, and/or cyanation.

As used herein, the term "peptide" or "polypeptide" is a linked sequence of amino acids and can be natural, recombinant, synthetic, or a modification or combination of natural, synthetic, and recombinant.

As used herein, the expression "effective amount" or "therapeutically effective amount" refers to an amount of the compound of the present disclosure that is effective to achieve a desired therapeutic result, such as, for example, the prevention, amelioration, or prophylaxis of an autoimmune disease or inflammatory condition. The compound of the present disclosure can be administered as a pharmaceutical composition comprising a therapeutically effective amount of the compound together with a pharmaceutically acceptable carrier. In the context of the present disclosure, a "therapeutically effective amount" is understood as the amount of a compound inhibiting the synthesis, expression, and/or activity of an identified HA polymer that is necessary to achieve the desired effect which, in this specific case, is treating an autoimmune disease or disorder, in particular, multiple sclerosis. Generally, the therapeutically effective amount of the compound according to the present disclosure to be administered will depend, among other factors, on the individual to be treated, on the severity of the disease the individual suffers, on the chosen dosage form, and the like. For this reason, the doses mentioned in the present disclosure must be considered only as a guideline for a person skilled in the art, and the skilled person must adjust the doses according to the previously mentioned variables. Nonetheless, a compound according to the present disclosure can be administered one or more times a day, for example, 1, 2, 3 or 4 times a day, in a typical total daily amount comprised between 0.1 μg to 10,000 mg/day, typically 100 to 1,500 mg/day.

The subject can be a human or non-human animal, a vertebrate, and is typically an animal, including but not limited to, cows, pigs, horses, chickens, cats, dogs, and the like. More typically, the subject is a mammal, and in a particular embodiment, human.

As used herein, an "autoimmune disease" is a disease or disorder arising from and directed against an individual's own tissues. The absence or depletion of Treg can lead to autoimmune disease. Examples of autoimmune diseases or disorders include, but are not limited to, multiple sclerosis, arthritis (rheumatoid arthritis, juvenile rheumatoid arthritis, psoriatic arthritis), conditions involving infiltration of T-cells and chronic inflammatory responses, autoimmune myocarditis, pemphigus, T1D (also referred to as autoimmune diabetes or insulin-dependent diabetes mellitus, autoimmune lung disease, primary sclerosing cholangitis, autoimmune thyroid disease, autoimmune liver disease, lupus, rheumatoid arthritis, eczema, Sjögrens disease, lichen planus, and the like.

As used herein the term "treating" or "treatment" means the administration of a compound according to the disclosure to effectively prevent, repress, ameliorate, or eliminate at least one symptom associated with inflammatory, autoimmune, allergic, or atopic disease, including, for example, T1D, T2D, MS, Sjögrens disease, autoimmune thyroiditis, primary sclerosing cholangitis, rheumatoid arthritis, psoriasis, colitis, lichen planus, psoriasis, eczema, and asthma. Preventing at least one symptom involves administering a treatment to a subject prior to onset of the symptoms associated with clinical disease. Repressing at least one symptom involves administering a treatment to a subject after clinical appearance of the disease.

As used herein, the term "a subject suffering from autoimmune diabetes" refers to a subject suffering from an autoimmune disease that results in a high blood glucose level which can lead to serious problems with the heart, eyes, kidneys, nerves, and gums and teeth. Symptoms of autoimmune diabetes include, for example, being very thirsty, urinating often, feeling very hungry or tired, losing weight without trying, having sores that heal slowly, having dry, itchy skin, losing the feeling in the feet or having tingling in the feet, and/or having blurry eyesight.

As used herein, the term "a subject suffering from multiple sclerosis" refers to a subject suffering from an autoimmune disease that results in damage to the insulating covers of nerve cells in the brain and spinal cord or demyelination. Symptoms of MS include numbness or weakness in one or more limbs, partial or complete loss of central vision, usually in one eye, often with pain during eye movement (optic neuritis), double vision or blurring of vision, tingling or pain in parts of the body, electric-shock sensations that occur with certain head movements, tremor, lack of coordination or unsteady gait, slurred speech, fatigue, dizziness, and/or heat sensitivity, among others.

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds of the disclosure are stable. As used herein "stable" refers to a compound that is sufficiently robust to survive isolation to a useful degree of purity from a reaction mixture.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

"Optionally substituted" groups can refer to, for example, functional groups that can be substituted or unsubstituted by additional functional groups. For example, when a group is unsubstituted, it can be referred to as the group name, for example alkyl or aryl. When a group is substituted with additional functional groups, it can more generically be referred to as substituted alkyl or substituted aryl.

As used herein, the term "alkyl" is meant to refer to a saturated hydrocarbon group which is straight-chained (e.g., linear) or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 30, from 1 to about 24, from 2 to about 24, from 1 to about 20, from 2 to about 20, from 1 to about 10, from 1 to about 8, from 1 to about 6, from 1 to about 4, or from 1 to about 3 carbon atoms.

As used herein, the term "alkylene" refers to a linking alkyl group.

As used herein, "alkenyl" refers to an alkyl group having one or more double carbon-carbon bonds. The alkenyl group can be linear or branched. Example alkenyl groups include ethenyl, propenyl, and the like. An alkenyl group can contain from 2 to about 30, from 2 to about 24, from 2 to about 20, from 2 to about 10, from 2 to about 8, from 2 to about 6, or from 2 to about 4 carbon atoms.

As used herein, "alkenylene" refers to a linking alkenyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "haloalkylene" refers to a linking haloalkyl group.

As used herein, "haloalkenyl" refers to an alkenyl group having one or more halogen substituents.

As used herein, "haloalkenylene" refers to a linking haloalkenyl group.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "arylene" refers to a linking aryl group.

As used herein, a "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heteroarylene" refers to a linking heteroaryl group.

As used herein, "acyl" refers to any group or organic radical such as H, alkyl, or alkenyl (the alkyl or alkenyl can be further substituted with an alkyl, alkoxy, cycloalkylamino, hydroxy, or halo) attached to a carbonyl (C=O) moiety. The acyl group is attached to the parent structure through the carbonyl moiety.

As used herein, "heteroalkyl" refers to an alkyl group having at least one heteroatom such as sulfur, oxygen, or nitrogen.

As used herein, "heteroalkylene" refers to a linking heteroalkyl group.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an —O-(haloalkyl) group.

As used herein, "cyano" refers to a —CN group.

As used herein, "nitro" refers to a —$NO_2$ group.

The compounds described herein can be asymmetric (e.g., having one or more stereocenters). All stereoisomers, such as enantiomers and diastereomers, are intended unless otherwise indicated.

Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and can be isolated as a mixture of isomers or as separated isomeric forms.

Compounds of the disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the disclosure can also include all isotopes of atoms occurring in the intermediates or final compounds. Isotopes include those atoms having the same atomic number but different mass numbers. For example, isotopes of hydrogen include tritium and deuterium.

In some embodiments, the compounds of the disclosure, and salts thereof, are substantially isolated. By "substantially isolated" is meant that the compound is at least partially or substantially separated from the environment in which it was formed or detected. Partial separation can include, for example, a composition enriched in the compound of the disclosure. Substantial separation can include compositions containing at least about 50%, at least about 60%, at least about 70%, at least about 80%, at least about 90%, at least about 95%, at least about 97%, or at least about 99% by weight of the compound of the disclosure, or salt thereof. Methods for isolating compounds and their salts are routine in the art.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

4-MUG Derivatives

The 4-methylumbelliferone glucuronide (4-MUG) derivatives of the present disclosure include a compound of Formula (I):

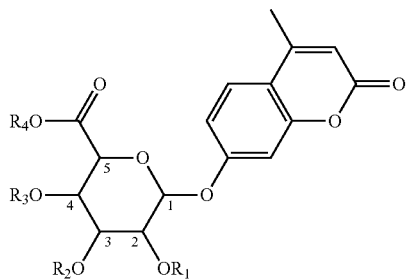

(I)

wherein $R_1$ and $R_2$ are each independently selected from H, C(O)—$C_{1-10}$ alkyl, and C(O)—$C_{1-10}$ haloalkyl;

$R_3$ is selected from H, C(O)—$C_{1-10}$ alkyl, C(O)—$C_{1-10}$ haloalkyl, C(O)—$C_{6-10}$ aryl, and C(O)—$C_{5-10}$ heteroaryl, wherein the C(O)—$C_{1-10}$ haloalkyl, C(O)—$C_{6-10}$ aryl, and C(O)—$C_{5-10}$ heteroaryl are each optionally substituted with 1, 2, 3, or 4 substituents independently selected from halo, cyano, and nitro; and $R_4$ is selected from $C_{2-10}$ alkyl and $C_{2-10}$ haloalkyl, or a pharmaceutically acceptable salt thereof.

The 1 to 5 carbon positions on the cyclic sugar moiety is indicated in Formula (I), above.

In some embodiments, $OR_1$ is in a down position at the 2-position in the cyclic sugar moiety:

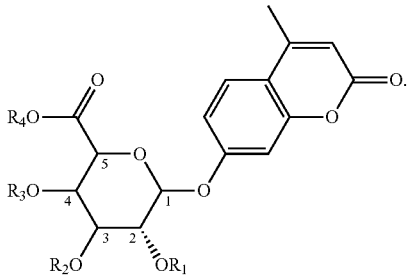

As used herein, the "up" or "down" position in a cyclic pyranose refers to the position of a substituent, for example, in a Haworth projection of the structures of the cyclic sugar, where the oxygen atom in the ring is drawn in the upper right-hand position of the hexagon, and the anomeric carbon refers to the 1-position in the cyclic sugar moiety. An up-position is oriented toward the top face of the ring, and the down position is oriented toward the bottom face of the ring.

In some embodiments, $OR_2$ is in an up position at the 3-position in the cyclic sugar moiety:

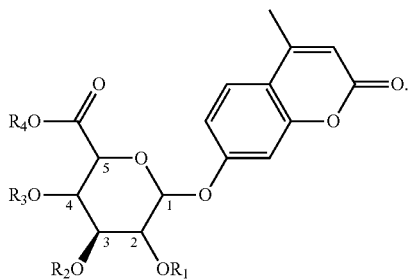

In some embodiments, $R_1$ and $R_2$ are each independently selected from H and C(O)—$C_{1-10}$ alkyl.

In some embodiments, $R_1$ and $R_2$ are each independently selected from H and C(O)—$C_{1-6}$ alkyl.

In some embodiments, $R_1$ and $R_2$ are each independently selected from H, C(O)-ethyl, and C(O)-methyl.

In some embodiments, $R_1$ and $R_2$ are each independently selected from H and C(O)-methyl.

In some embodiments, $OR_3$ is in a down position at the 4-position in the cyclic sugar moiety:

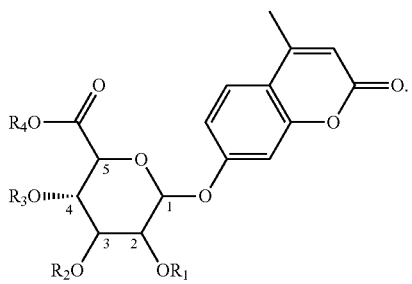

In some embodiments, $R_3$ is selected from H and C(O)—$C_{1-10}$ alkyl.

In some embodiments, $R_3$ is selected from H and C(O)—$C_{1-6}$ alkyl.

In some embodiments, $R_3$ is selected from H, C(O)-ethyl, and C(O)-methyl.

In some embodiments, $R_3$ is selected from H and C(O)-methyl.

In some embodiments, C(O)$OR_4$ is in an up position at the 5-position in the cyclic sugar moiety:

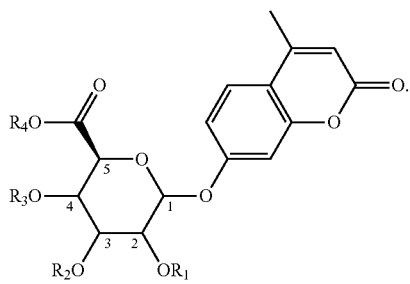

In some embodiments, R$_4$ is C$_{2-10}$ alkyl.

In some embodiments, R$_4$ is C$_{2-6}$ alkyl.

In some embodiments, R$_4$ is selected from ethyl, propyl, and butyl.

In some embodiments, R$_4$ is selected from ethyl and butyl.

In some embodiments, the 4-methylumbelliferone moiety is substituted in a β-anomeric position in the cyclic sugar moiety.

In some embodiments, the compound of Formula (I) is a 4-methylumbelliferone β-glucuronide:

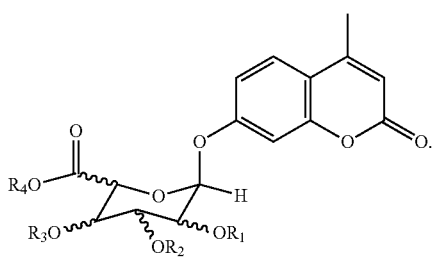

In some embodiments, the compound of claim 1 is selected from

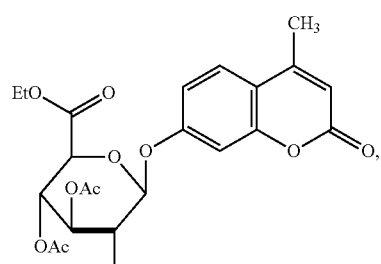

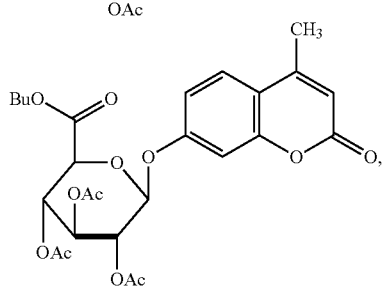

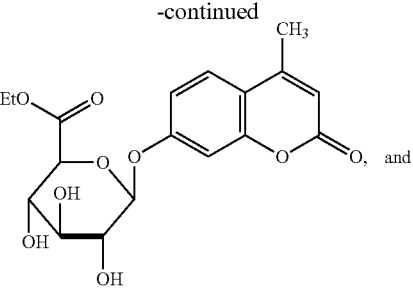

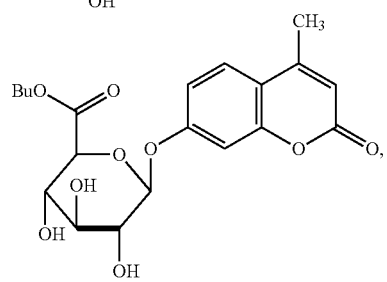

or a pharmaceutically acceptable salt thereof. As used herein, Bu refers to butyl, Et refers to ethyl, and Ac refers to acetyl.

In some embodiments, the present disclosure features a composition including a compound of Formula (I) as described above, or a pharmaceutically acceptable salt thereof, and a pharmaceutically acceptable carrier.

In some embodiments, the present disclosure features a method for intracellular delivery of a 4-methylumbelliferone-glucuronide derivative, including contacting a cell with a compound of Formula (I), or a pharmaceutically acceptable salt thereof, as described above.

In some embodiments, the present disclosure features a method of inducing a regulatory T-cell response, including administering to a subject a therapeutically effective amount of a compound of Formula (I), or a pharmaceutically acceptable salt thereof, as described above.

In some embodiments, the present disclosure features a method of inhibiting hyaluronan synthesis in a subject, including administering to the subject a therapeutically effective amount of a compound of Formula (I), or a pharmaceutically acceptable salt thereof, as described above.

In some embodiments, the present disclosure features a method of increasing FoxP3+ regulatory T-cells, including administering to a subject a therapeutically effective amount of a compound of Formula (I), or a pharmaceutically acceptable salt thereof, as described above.

In some embodiments, the present disclosure features a method of treating autoimmune, allergic, inflammatory, or atopic disease in a subject, including administering to the subject a therapeutically effective amount of a compound of Formula (I), or a pharmaceutically acceptable salt thereof, as described above. The autoimmune, allergic, or atopic disease can be selected from the group consisting of diabetes (type 1 and/or type 2), pre-diabetes, multiple sclerosis, Sjögrens disease, autoimmune thyroiditis, Lupus, rheumatoid arthritis, primary sclerosing cholangitis, psoriasis, colitis, eczema, and asthma.

In some embodiments, the present disclosure features a method for treating insulitis and/or reversing progression of autoimmune diabetes in a subject suffering from or at risk of developing autoimmune diabetes, the method including administering to the subject a composition including a compound of Formula (I), or a pharmaceutically acceptable salt thereof, in an amount effective to inhibit hyaluronan synthesis in the subject.

In some embodiments, the present disclosure features a method for treating multiple sclerosis in a subject in need thereof, the method including administering to the subject a composition including a compound of Formula (I), or a pharmaceutically acceptable salt thereof, in an amount effective to inhibit hyaluronan synthesis in the subject.

In some embodiments, the present disclosure features a method for treating multiple sclerosis and/or autoimmune demyelination in a subject suffering from or at risk of developing multiple sclerosis, the method including administering to the subject a composition comprising a compound of Formula (I), or a pharmaceutically acceptable salt thereof, in an amount effective to inhibit hyaluronan synthesis in the subject.

In some embodiments, the subject is a human.

Figure 10A:
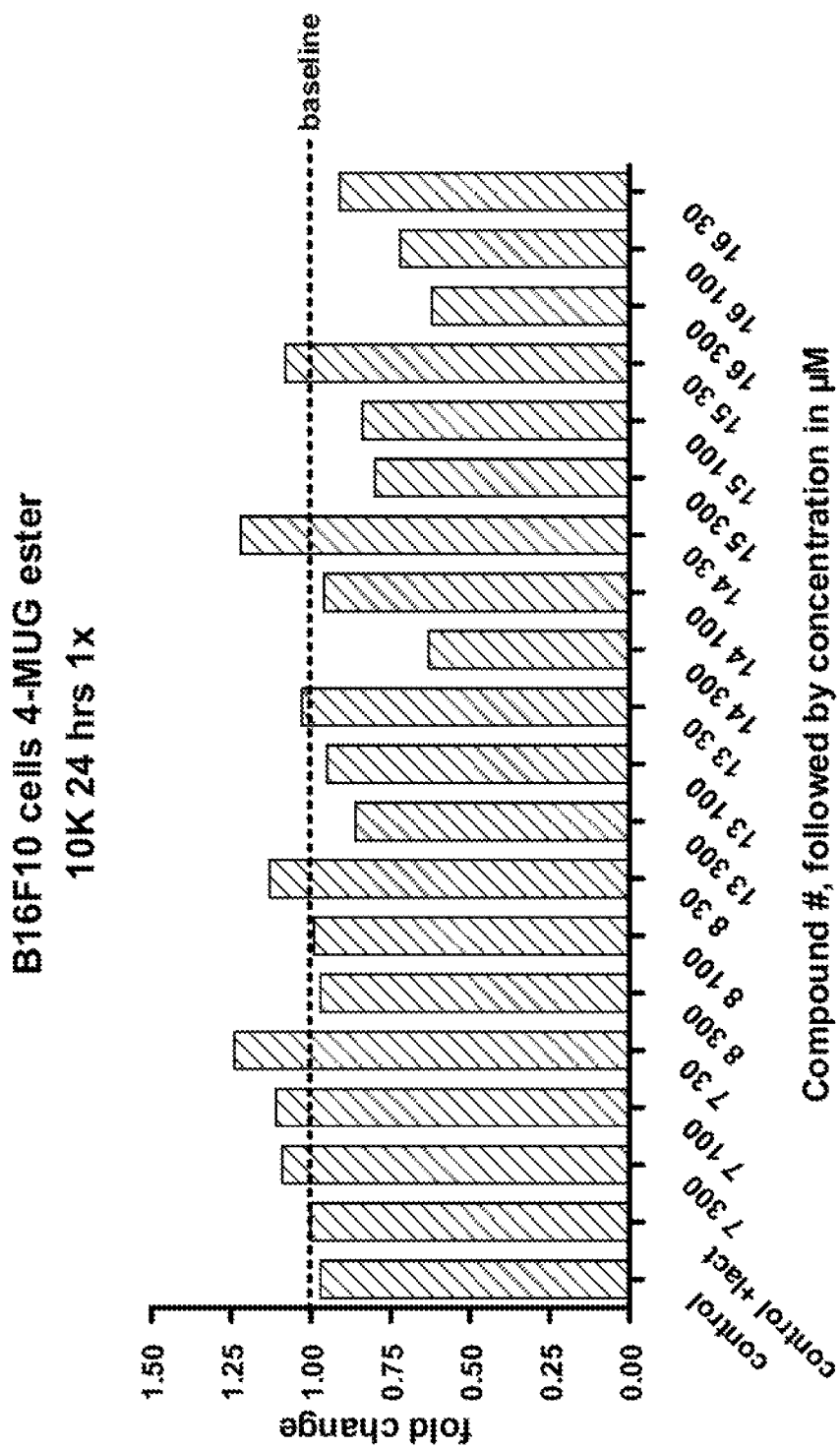
FIG. 10A is a graph showing that a dye which tags dead or dying cells, CellTag 700, is not substantially bound to B16 cells at 24 hours in the setting of treatment with embodiments of 4-MUG esters of the present disclosure, indicating that these compounds are not toxic.
Figure 10B:
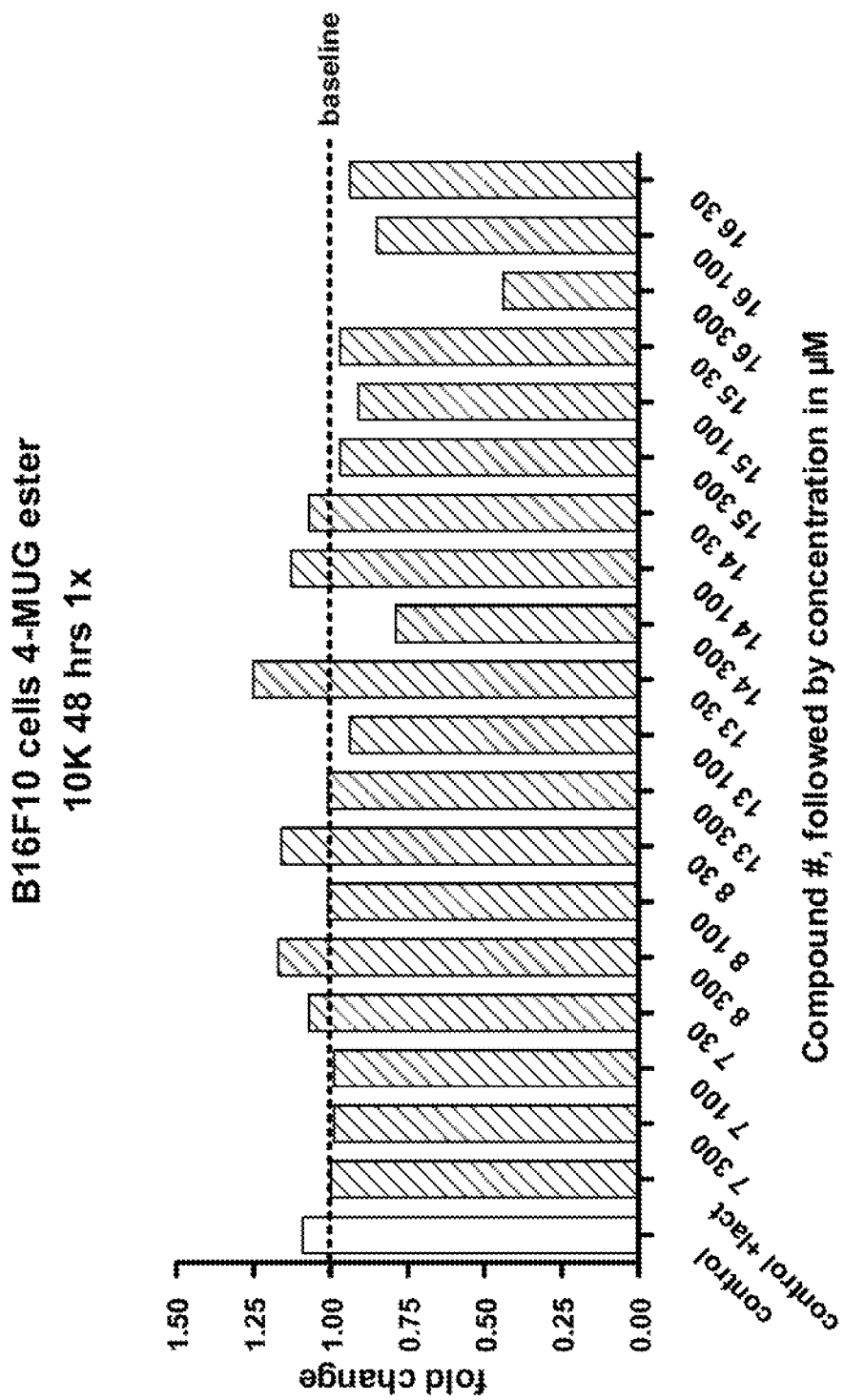
FIG. 10B is a graph showing that a dye which tags dead or dying cells, CellTag 700, is not substantially bound to B16 cells at 48 hours in the setting of treatment with embodiments of 4-MUG esters of the present disclosure, indicating that these compounds are not toxic.
Figure 10C:
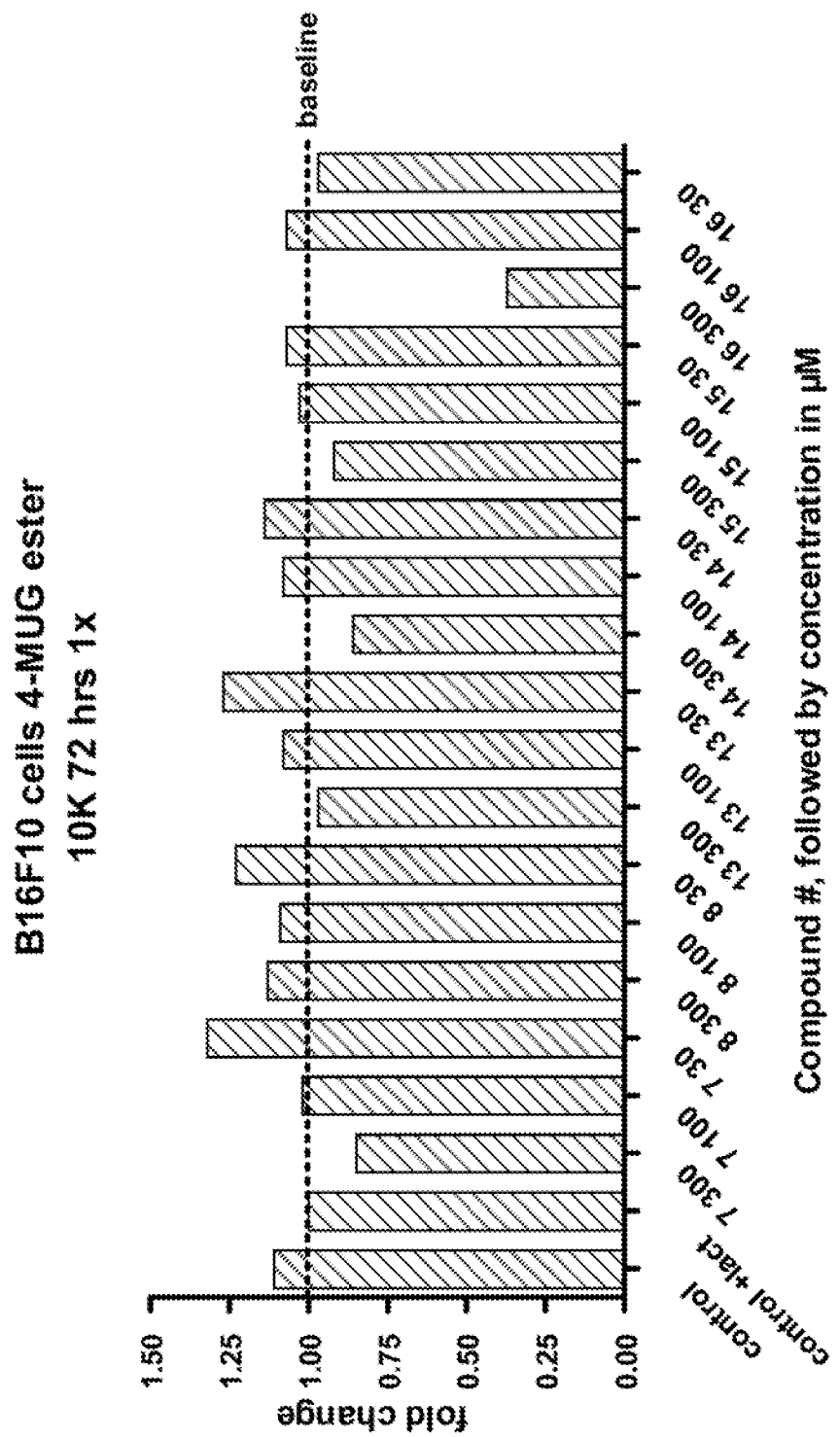
FIG. 10C is a graph showing that a dye which tags dead or dying cells, CellTag 700, is not substantially bound to B16 cells at 72 hours in the setting of treatment with embodiments of 4-MUG esters of the present disclosure, indicating that these compounds are not toxic.

A shown in FIG. 1, 4-MUG is a major metabolite of 4-MU. As will be described in EXAMPLE 1 below, 4-MUG and newly described derivatives of 4-MUG (FIG. 2) are pharmacologically active. Indeed, 4-MUG inhibits HA synthesis by human cell lines as well as 4-MU (FIGS. 3 and 4). The derivatives of 4-MUG of the present disclosure are likewise pharmacologically active (FIGS. 5-8). Not all derivatives of 4-MUG are active against HA synthesis (FIG. 9). These HA quantification results were all normalized to protein levels (FIGS. 10A-10C). This is an exciting and previously unknown finding that provides the possibility of delivering 4-MUG or 4-MUG derivatives as an agent to inhibit HA synthesis. It was previously assumed that 4-MUG was pharmacologically inactive and indeed all of the published bioavailability calculations that have been made in regards to 4-MU reflect this assumption (Garrett, E. R., et al., *Biopharm. Drug Dispos.* 14, 13-39 (1993); Garrett, E. R. and Venitz, J., *J Pharm Sci* 83, 115-116 (1994)).

The manner in which 4-MUG inhibits HA synthesis is unclear. Typically, glucuronidation is a metabolic step that promotes the excretion and clearance of most drugs. Indeed, because glucuronidated compounds are often more water soluble, they typically do not enter cells as well as more lipophilic parent compounds. Thus, it is surprising and not intuitive that the 4-MUG or its derivatives would inhibit HA synthesis.

It was previously reported that 4-MU promotes induction of FoxP3+ regulatory T-cells (Nagy, N. et al., *J. Clin. Invest.* 125, 10.1172/JCI79271-0 (2015); Kuipers, H. F. et al., *Proc. Natl. Acad. Sci. U.S.A.* 113, 1339-1344 (2016); Nagy, N. et al., *Front. Immunol.* 6, 123 (2015)), a critical cell type that promotes immune tolerance in multiple tissues and disease states (Sakaguchi, S., et al., *Nat. Rev. Immunol.* 10, 490-500 (2010)). In the present disclosure, it was observed that 4-MUG also has this property in vivo (FIG. 11).

In light of these data, 4-MUG and its derivatives can reduce or inhibit systemic HA synthesis and reduce or prevent inflammatory, autoimmune, allergic, or atopic disease in a subject.

Compositions

In another aspect, the present disclosure provides compositions that include the compounds of the disclosure. The compositions include one or more compounds of the disclosure, optionally one or more additional therapeutic agents, and a medium (e.g., a lipophilic medium). Representative lipophilic medium includes the following:

Fatty acids and esters thereof, including carboxylic acids of various chain lengths, mostly straight chain, but which could be branched, examples of which include capric, caprylic, caproic, lauric, myristic, stearic, oleic, linoleic, behenic, and as well as saturated or unsaturated fatty acids and esters;

Fatty acids esterified with glycerin to form mono-, di-, or triglycerides, which can be synthetic or derived from natural sources, including, but not limited to, for example, glycerides such as soybean oil, cottonseed oil, rapeseed oil, fish oil, castor oil, Capmul® MCM, Captex® 300, Miglyol® 812, glyceryl monooleate, triacetin, acetylated monoglyceride, tristearin, glyceryl behenate, and diacetyl tartaric acid esters of monoglycerides;

Glycerides conjugated to other moieties, such as polyethylene glycol (for example, Labrasol®, Labrafac™, Cremophor® EL);

Phospholipids, either natural or synthetic, such as dimyristyl phosphatidylcholine, egg lecithin, and pegylated phospholipids;

Other fatty esters including fatty alcohols (myristyl myristate, isopropyl palmitate), or sugars (sorbitan monooleate, SPAN® 80, Tween 80, sucrose laurate);

Fatty alcohols such as stearyl alcohol, lauryl alcohol, benzyl alcohol, or esters or ethers thereof, such as benzyl benzoate;

Organic co-solvents can also be used in the compositions, optionally in combination with water, including for example, ethanol, polyethylene glycol, propylene glycol, glycerol, N-methyl pyrrolidone, and dimethyl sulfoxide.

Compositions and Methods of Use

In a further aspect, the disclosure provides emulsion, microemulsion, and micelle formulations that include a compound of the disclosure. Methods for making the emulsion, microemulsion, and micelle formulations are also provided.

As used herein, the term "emulsion" refers to a colloidal dispersion of two immiscible liquids, such as an oil and water, in the form of droplets, whose diameter, in general, are between 0.1 and 3.0 microns and which is typically optically opaque, unless the dispersed and continuous phases are refractive index matched. Such systems possess a finite stability, generally defined by the application or relevant reference system, which can be enhanced by the addition of amphiphilic molecules or viscosity enhancers.

The term "microemulsion" refers to a thermodynamically stable isotropically clear dispersion of two immiscible liquids, such as an oil and water, stabilized by an interfacial film of surfactant molecules. The microemulsion has a mean droplet diameter of less than 200 nm, in general between 10-50 nm. In the absence of water, mixtures of oil(s) and non-ionic surfactant(s) form clear and isotropic solutions that are known as self-emulsifying drug delivery systems (SEDDS) and can be used to improve lipophilic drug dissolution and oral absorption.

The emulsion and microemulsion formulations include an oil phase and an aqueous phase. The emulsion or microemulsion can be an oil-in-water emulsion or a water-in-oil emulsion. The oil phase includes one or more compounds of the disclosure and a lipophilic medium, as described above. In one embodiment, the compound is present in the formulation in an amount from about 0.005 to about 3.0 weight percent based on the total weight of the formulation. In one embodiment, the compound is present in the formulation in an amount from about 0.01 to about 2.5 weight percent based on the total weight of the formulation. In one embodiment, the compound is present in the formulation in an amount from about 0.1 to about 1.5 weight percent based on the total weight of the formulation. In one embodiment, the lipophilic medium is present in the formulation in an amount from about 2 to about 20 weight percent based on the total weight of the formulation. In one embodiment, the lipophilic medium is present in the formulation in an amount from about 4 to about 12 weight percent based on the total weight of the formulation. In one embodiment, the lipophilic medium is present in the formulation in an amount from about 6 to about 10 weight percent based on the total weight of the formulation.

In addition to the compounds of the disclosure, the emulsion or microemulsion formulations can include other components commonly used in emulsions and microemulsions, and particularly used in pharmaceutical emulsions and microemulsions. These components include surfactants and co-solvents, among others.

Suitable nonionic surfactants include block copolymers of ethylene oxide and propylene oxide known as POLOXAMERS or PLUROINICS®. These synthetic block copolymers of having the general structure: $H(OCH_2CH_2)_a(OC_3H_6CH_2)_b(OCH_2CH_2)_aOH$. The following variants based on the values of a and b are commercially available from BASF Performance Chemicals (Parsippany, N.J.) under the trade name PLURONIC® and consist of the group of surfactants designated by the CTFA name of POLOXAMER 108, 188, 217, 237, 238, 288, 338, 407, 101, 105, 122, 123, 124, 181, 182, 183, 184, 212, 231, 282, 331, 401, 402, 185, 215, 234, 235, 284, 333, 334, 335, and 403. For the most commonly used POLOXAMERS 124, 188, 237, 338, and 407 the values of a and b are 12/20, 79/28, 64/37, 141/44 and 101/56, respectively. In one embodiment the nonionic surfactant is present in the formulation in an amount from about 0.5 to about 5 weight percent based on the total weight of the formulation.

Co-solvents useful in the formulations include ethanol, polyethylene glycol, propylene glycol, glycerol, N-methylpyrrolidone, dimethylamide, and dimethylsulfoxide, among others. Polyethylene glycol (PEG) is a hydrophilic, polymerized form of ethylene glycol, consisting of repeating units having the chemical structure: ($-CH_2CH_2O-$). The general formula for polyethylene glycol is $H(OCH_2CH_2)_nOH$. The molecular weight ranges from 200 to 10,000. Such various forms are described by their molecular weights, for example, PEG-200, PEG-300, PEG-400, and the like.

In a further aspect, the disclosure provides micelle formulations that include a compound of the disclosure and an aqueous phase. Micelles are organized aggregates of one or more surfactants in solution. In one embodiment, the compound is present in the formulation in an amount from about 0.005 to about 3.0 weight percent based on the total weight of the formulation. In one embodiment, the compound is present in the formulation in an amount from about 0.01 to about 2.5 weight percent based on the total weight of the formulation. In one embodiment, the compound is present in the formulation in an amount from about 0.1 to about 1.0 weight percent based on the total weight of the formulation. Suitable surfactants include those noted above, and in the amounts noted above.

The micelle formulation can also include additional components such as co-solvents including those noted above. In one embodiment, the micelle formulation includes a polyethylene glycol and a lower alkyl alcohol (e.g., ethanol). In one embodiment, the co-solvents are present in an amount from about 2 to about 20 weight percent based on the total weight of the formulation. The micelle, emulsion, and microemulsion formulations include an aqueous phase. In one embodiment, the aqueous phase includes deionized water. In another embodiment, the aqueous phase includes saline. In another embodiment, the aqueous phase is saline buffered with an organic acid (e.g., succinate, citrate).

The disclosure also provides the use of the compounds of the disclosure in the manufacture of a medicament, for example, for the treatment of cell proliferative disease.

In other aspects, methods for administering a compound of the disclosure to a subject in need thereof, and methods for treating a condition treatable by administration of a therapeutically effective amount of a compound of the disclosure are also provided. These methods include the administration of the compounds, compositions, emulsion formulations, microemulsion formulations, and micelle formulations described herein.

In one embodiment, the disclosure provides a method for treating a condition that is treatable by the parent, unmodified nucleoside or nucleoside analogue (e.g., a cell proliferative disease such as cancer). In the method, a therapeutically effective amount of a compound of the disclosure is administered to a subject in need thereof.

In one embodiment, the disclosure provides a method for intracellular delivery of a monophosphorylated nucleoside or nucleoside analogue. In the method, a compound of the disclosure is contacted with a cell. When internalized into a cell, the compound is cleaved by cellular enzymes (e.g., phosphatase and/or phosphodiesterase) into the corresponding nucleoside or nucleoside analogue phosphate, and tocopherol or tocotrienol.

In one embodiment, the disclosure provides a method for treating a cell proliferative disease by administering a compound of the disclosure having a nucleoside or nucleoside analogue derived from a therapeutic drug effective in treating cell proliferative disease. Representative cell proliferative diseases treatable by the compounds of the disclosure include hematologic cancers, such as leukemia, lymphoma, and myeloma; and nonhematologic cancers, such as solid tumor carcinomas (e.g., breast, ovarian, pancreatic, colon, colorectal, lung (e.g., non-small cell lung), and bladder), sarcomas, and gliomas.

Therapeutically effective amounts of the compounds will generally range up to the maximally tolerated dosage, but the concentrations are not critical and can vary widely. The precise amounts employed by the attending physician will vary, of course, depending on the compound, route of administration, physical condition of the patient and other factors. The daily dosage can be administered as a single dosage or can be divided into multiple doses for administration.

The amount of the compound actually administered will be a therapeutically effective amount, which term is used herein to denote the amount needed to produce a substantial beneficial effect. Effective doses can be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art. Thus, the amount actually administered will be dependent upon the individual to which treatment is to be applied, and will preferably be an optimized amount such that the desired effect is achieved without significant side-effects.

Therapeutic efficacy and possible toxicity of the compounds of the disclosure can be determined by standard pharmaceutical procedures, in cell cultures or experimental animals (e.g., ED50, the dose therapeutically effective in 50% of the population; and LD50, the dose lethal to 50% of the population). The dose ratio between therapeutic and toxic effects is the therapeutic index, and it can be expressed as the ratio LD50 to ED50. Modified therapeutic drug compounds that exhibit large therapeutic indices are particularly suitable in the practice of the methods of the disclosure. The data obtained from cell culture assays and animal studies can be used in formulating a range of dosage for use in humans or other mammals. The dosage of such compounds lies preferably within a range of circulating concentrations that include the ED50 with little or no toxicity. The dosage typically varies within this range depending upon the dosage form employed, sensitivity of the patient, and the route of administration. Thus, optimal amounts will vary with the method of administration, and will generally be in accordance with the amounts of conventional medicaments administered in the same or a similar form.

The compounds of the disclosure can be administered alone, or in combination with one or more additional therapeutic agents. Appropriate amounts in each case will vary with the particular agent, and will be either readily known to those skilled in the art or readily determinable by routine experimentation.

Administration of the compounds of the disclosure is accomplished by any effective route, for example, parenteral, topical, or oral routes. Methods of administration include inhalational, buccal, intramedullary, intravenous, intranasal, intrarectal, intraocular, intraabdominal, intraarterial, intraarticular, intracapsular, intracervical, intracranial, intraductal, intradural, intralesional, intramuscular, intralumbar, intramural, intraocular, intraoperative, intraparietal, intraperitoneal, intrapleural, intrapulmonary, intraspinal, intrathoracic, intratracheal, intratympanic, intrauterine, intravascular, and intraventricular administration, and other conventional means. The compounds of the disclosure having anti-tumor activity can be injected directly into a tumor, into the vicinity of a tumor, into a blood vessel that supplies blood to the tumor, or into lymph nodes or lymph ducts draining into or out of a tumor.

The emulsion, microemulsion, and micelle formulations of the disclosure can be nebulized using suitable aerosol propellants that are known in the art for pulmonary delivery of the compounds.

The compounds of the disclosure can be formulated into a composition that additionally comprises suitable pharmaceutically acceptable carriers, including excipients and other compounds that facilitate administration of the compound to a subject. Further details on techniques for formulation and administration can be found in the latest edition of "Remington's Pharmaceutical Sciences" (Maack Publishing Co., Easton, Pa.).

Compositions for oral administration can be formulated using pharmaceutically acceptable carriers well known in the art, in dosages suitable for oral administration. Such carriers enable the compositions containing the compounds of the disclosure to be formulated as tablets, pills, dragees, capsules, liquids, gels, syrups, slurries, suspensions, suitable for ingestion by a subject. Compositions for oral use can be formulated, for example, in combination with a solid excipient, optionally grinding the resulting mixture, and processing the mixture of granules, after adding suitable additional compounds, if desired, to obtain tablets or dragee cores. Suitable excipients include carbohydrate or protein fillers. These include, but are not limited to, sugars, including lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins, such as gelatin and collagen. If desired, disintegrating or solubilizing agents can be added, such as the crosslinked polyvinyl pyrrolidone, agar, alginic acid, or a salt thereof, such as sodium alginate.

Dragee cores are provided with suitable coatings such as concentrated sugar solutions, which can also contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound (i.e., dosage).

Compounds for oral administration can be formulated, for example, as push-fit capsules made of gelatin, as well as soft, sealed capsules made of gelatin and a coating such as glycerol or sorbitol. Push-fit capsules can contain the compounds mixed with filler or binders such as lactose or starches, lubricants such as talc or magnesium stearate, and, optionally, stabilizers. In soft capsules, the covalent conjugates can be dissolved or suspended in suitable liquids, such as fatty oils, liquid paraffin, or liquid polyethylene glycol with or without stabilizers.

For topical or nasal administration, penetrants appropriate to the particular barrier to be permeated are typically used in the formulation. Examples of these are 2-pyrrolidone, N-methyl-2-pyrrolidone, dimethylacetamide, dimethyl-formamide, propylene glycol, methyl or isopropyl alcohol, dimethyl sulfoxide, and azone. Additional agents can further be included to make the formulation cosmetically acceptable. Examples of these are fats, waxes, oils, dyes, fragrances, preservatives, stabilizers, and surface-active agents. Keratolytic agents such as those known in the art can also be included. Examples are salicylic acid and sulfur. For topical administration, the composition can be in the form of a transdermal ointment or patch for systemic delivery of the compound and can be prepared in a conventional manner (see, e.g., Barry, Dermatological Formulations (Drugs and the Pharmaceutical Sciences—Dekker); Harry's Cosmeticology (Leonard Hill Books).

For rectal administration, the compositions can be administered in the form of suppositories or retention enemas. Such compositions can be prepared by mixing the compounds with a suitable non-irritating excipient that is solid at ordinary temperatures but liquid at the rectal temperature and will therefore melt in the rectum to release the drug. Suitable excipients include, but are not limited to, cocoa butter and polyethylene glycols.

The amounts of each of these various types of additives will be readily apparent to those skilled in the art, optimal amounts being the same as in other, known formulations designed for the same type of administration.

Compositions containing the compounds of the disclosure can be manufactured in a manner similar to that known in the art (e.g., by means of conventional mixing, dissolving, granulating, dragee-making, levigating, emulsifying, encapsulating, entrapping or lyophilizing processes). The compositions can also be modified to provide appropriate release characteristics, sustained release, or targeted release, by conventional means (e.g., coating). As noted above, in one embodiment, the compounds are formulated as an emulsion.

Compositions containing the compounds can be provided as a salt and can be formed with many acids, including but not limited to hydrochloric, sulfuric, acetic, lactic, tartaric, malic, and succinic. Salts tend to be more soluble in aqueous or other protonic solvents than are the corresponding free base forms.

After compositions formulated to contain a compound and an acceptable carrier have been prepared, they can be placed in an appropriate container and labeled for use. Thus, in another aspect, the disclosure provides kits.

As will be shown in EXAMPLE 1 below, an oral drug that promotes Treg induction in vivo is demonstrated. 4-MUG and its pro-drugs could be a powerful tool to promote immune tolerance. Inhibition of HA synthesis can be an effective strategy to treat inflammation. HA is an inflammatory mediator that is not currently targeted pharmacologically. 4-MUG can be a potential treatment for other autoimmunity, cancer metastasis, and other indications. HA deposits are present in multiple chronic inflammatory diseases, including multiple sclerosis, rheumatoid arthritis, juvenile idiopathic arthritis (Yoshioka, Y. et al., *Arthritis Rheum.* 65, 1160-1170 (2013)) and lupus nephritis (Yung S., et al., *Hindawi* 2012, 207190-9 (2012)). EXAMPLE 2 below shows that embodiments of the compounds of the present disclosure, such as butyl-4-MUG, surprisingly delays the onset of diabetes at $\frac{1}{100}^{th}$ the dose of 4-MU.

EXAMPLE 1

Treg Induction In Vivo by 4-MUG and 4-MUG Prodrugs

B16F10 Cells

B16F10 is a murine melanoma cell line. The cells are adherent and the cell morphology shows a mixture of spindle-shaped and epithelial-like cells. The cells were cultured at 37° C. temperature and an atmosphere of 95% air and 5% carbon dioxide. Cells were cultured in DMEM plus 10% FBS.

For the 4-MUG ester experiments, cells were seeded in 48-well plates, at a density of 10,000 cells per well and cultured for 24-72 hours. 4-MU, 4-MUG and the 4-MUG esters were diluted 1:1000 from their stock concentration and added to the cell medium in their final μM concentrations.

For the analysis, the cells and the cell supernatant were collected at the end of each experiment and stored at −20° C. until further use.

Cell Lysis 48-well plates from previous experiments were thawed and 200 μL cell lysis buffer was added to each well. Cells were incubated for 15 minutes at room temperature. The whole lysate was transferred into a 96-well v-bottom plate and centrifuged at 3500 g for 20 minutes at 4° C. After spinning 25 μL from each well was transferred into a flat-bottom 96-well plate and stored until further use. Cell lysis buffer contains Tris-HCl, EDTA, SDS, $MgCl_2$ and Super Nucleasis®.

Protein Measurement

Protein measurement was performed by using the Pierce BCA Protein Assay Kit® (Thermo Scientific) according to the manufacturer instructions. The BCA Protein assay is based on bicinchoninic acid (BCA) for the colorimetric detection and quantitation of total protein. This method combines a biuret reaction (reduction of $Cu2+$ to $Cu1+$ by protein in an alkaline medium) with a highly and selective colorimetric detection of the cuprous cation ($Cu1+$) with the help of bicinchoninic acid. A purple-colored reaction product is formed by the chelation of two BCA molecules with one cuprous ion. This complex has a strong absorbance at 562 nm.

LI-COR CellTag™ 700 Cell Number Normalization

The CellTag 700 stain is a near-infrared fluorescent, non-specific cell stain that provides accurate normalization to cell number. The stain accumulates in both the nucleus and cytoplasm of permeabilized cells, and provides linear fluorescent signal across a wide range of cell types and cell numbers. CellTag 700 is detected in the 700 nm channel of the Odyssey® Imaging System.

Cells were fixed with 4% formaldehyde for 30 minutes at room temperature and afterwards permeabilized with 0.1% Triton X-100 in PBS. Cells were washed five times with PBS and 0.1% Tween 20. Subsequently 0.2 uM CellTag 700 stain was added to the cells for 60 min. Cells were washed again with PBS containing 0.1% Tween 20 five times for 5 minutes. Next the plate was scanned in the 700 nm channel of the Odyssey Infrared Imaging System.

Hyaluronan (HA) ELISA

The identification of HA in the samples is achieved by utilizing a highly specific HA binding protein (HABP) probe that interacts with HA. The HABP is prepared by enzymatic digestion of the chondroitin sulfate proteoglycan aggrecan present in bovine nasal cartilage. The HA concentration in the tissue is determined by using an ELISA-like assay.

96-well plates were coated with HA-BSA for 1 hour at room temperature. Samples and standards were prepared with HABP for the assay. The plate was washed after coating three times with PBS, and blocked with 10% FBS in PBS for 1 hour at room temperature. The plate was washed after blocking again with three times PBS, subsequently standards and samples were transferred onto the plate for 1 hour. The plate was washed after sample transfer four times with nanopure water. Afterwards the plate was incubated with Streptavidin-HRP for 20 minutes and washed four times with nanopure water. After washing the plate was incubated with TMB substrate for 5-20 minutes, time depending on the intensity of the developing color. In order to stop the TMB reaction, sulfuric acid was applied to the plate. The plate was read at 405 nm and the concentrations were calculated according to the standards.

Cell Staining

B16 cells were stained for phalloidin and the nuclei were visualized with DAPI. Phalloidin was used to visualize the distribution of F-actin, and DAPI was used to visualize the nuclei. Unlike the usual antibodies, DAPI emits a blue fluorescence upon binding to AT regions of DNA.

The cells were fixed with 4% formaldehyde for 20 minutes at room temperature. After fixation cells were washed three times for 5 minutes in PBS and permeabilized with 0.1% Triton X in PBS for 2 minutes. After permeabilization cells were washed again and subsequently stained for F-actin and nuclei. Cells were stained with a 50 μg/mL phalloidin solution in PBS for 40 minutes at room temperature. The staining solution was removed and the cells were washed three times for 5 minutes with PBS. Nuclei were stained for 2 minutes with a 300 nM DAPI solution, the staining solution was removed and the cells were washed three times for 5 minutes with PBS. The whole staining process was carried out protected from light.

4-MUG and newly described derivatives of 4-MUG (FIG. 2) are pharmacologically active. Indeed, 4-MUG inhibits HA synthesis by human cell lines as well as 4-MU (FIGS. 3 and 4). The derivatives of 4-MUG of the present disclosure are likewise pharmacologically active (FIGS. 5-8). Not all derivatives of 4-MUG are active against HA synthesis (FIG. 9). These HA quantification results were all normalized to protein levels using LI-COR CellTag™ 700 cell number normalization in B16 cells after exposure to 4 MUG ester. FIGS. 10A-10C shows that a dye which tags dead or dying cells, CellTag 700, is not substantially bound to B16 cells in the setting of treatment with these esters, indicating that these compounds are not toxic. Taken together, this is an exciting and previously unknown finding that provides the possibility of delivering 4-MUG or 4-MUG derivatives as an agent to inhibit HA synthesis.

The manner in which 4-MUG inhibits HA synthesis is unclear. Typically, glucuronidation is a metabolic step that promotes the excretion and clearance of most drugs. Indeed, because glucuronidated compounds are often more water soluble, they typically do not enter cells as well as more lipophilic parent compounds. Thus, it is surprising and not intuitive that the 4-MUG or its derivatives would inhibit HA synthesis.

It was previously reported that 4-MU promotes induction of FoxP3+ regulatory T-cells (Nagy, N. et al., *J. Clin. Invest.* 125, 10.1172/JCI79271-0 (2015); Kuipers, H. F. et al., *Proc. Natl. Acad. Sci. U.S.A.* 113, 1339-1344 (2016); Nagy, N. et al., *Front Immunol.* 6, 123 (2015)), a critical cell type that promotes immune tolerance in multiple tissues and disease states (Sakaguchi, S., et al., *Nat. Rev. Immunol.* 10, 490-500 (2010)). In the present disclosure, it was observed that 4-MUG also has this property in vivo. FIGS. 11A-11D graphically represent the induction of FoxP3+ regulatory T-cells by 4-MUG. 4-MUG does not increase the numbers of CD3+ T-cells (FIG. 11A), CD4+ T-cells (FIG. 11B), or CD25+ T-cells (FIG. 11C) but does increase the fraction of Foxp3+ regulatory T-cells (FIG. 11D). This indicates a specific effect on Foxp3+ T regulatory T-cells.

Figure 12B:
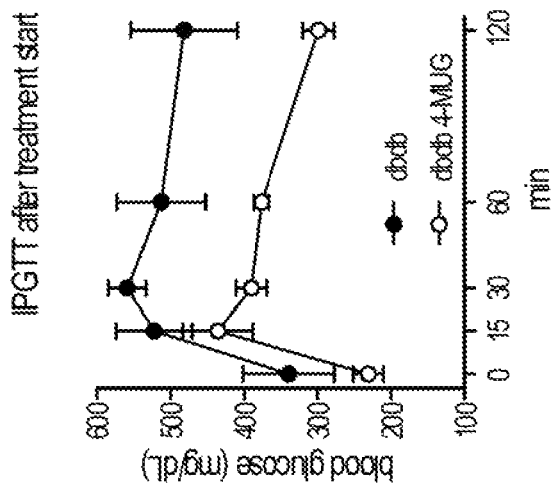
FIG. 12B graphically represents a blood glucose level over time in subjects following an intra-peritoneal glucose tolerance test (IPGTT).
Figure 12A:
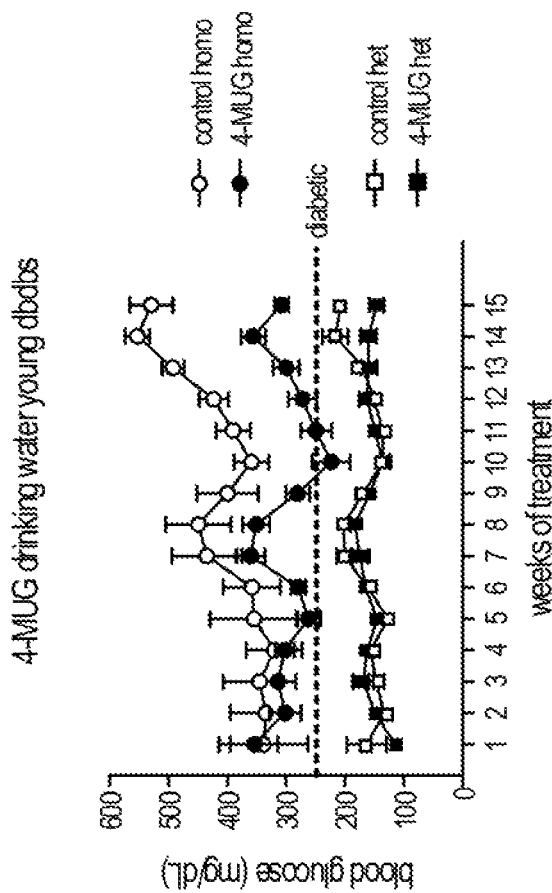
FIG. 12A graphically represents a blood glucose level over time in subjects administered 4-MUG.
Figure 13:
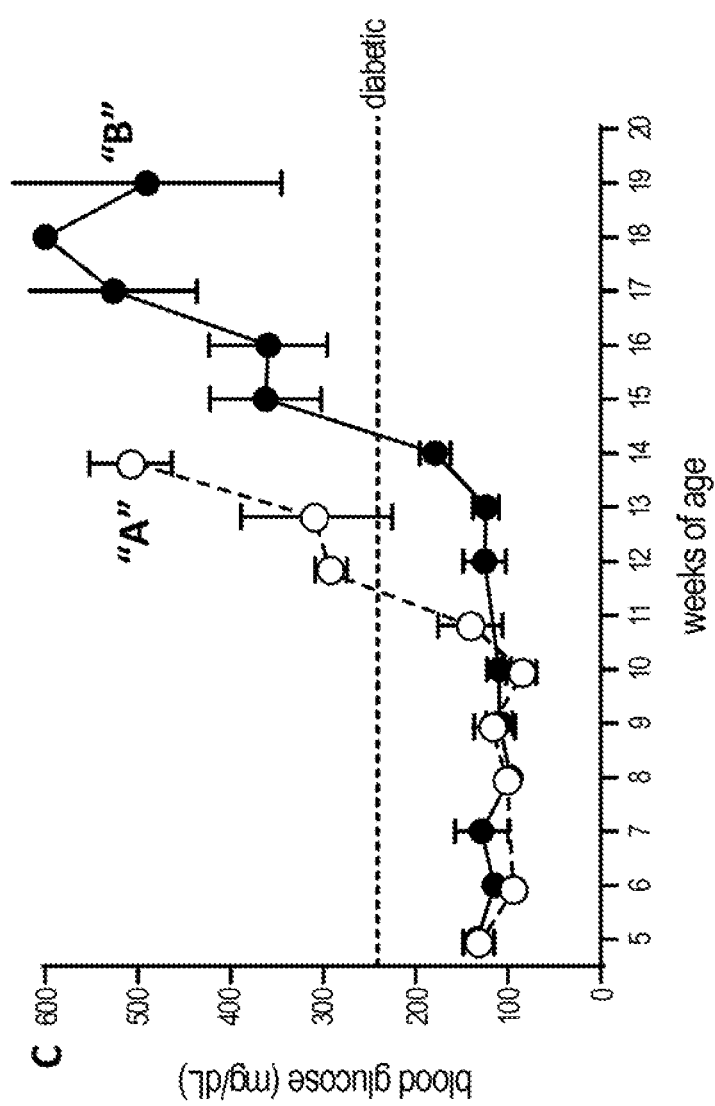
FIG. 13 is a graph showing onset of diabetes (above horizontal line at about 250 mg/dL blood glucose) in compound A or compound B-administered mice.

The impact of 4-MUG in drinking water on blood glucose (BG) of db/db mice, an established mouse model of type 2 diabetes was assessed. FIG. 12A graphically represents blood glucose levels in db/db mice maintained on 4-MUG in drinking water versus control water (n=5 mice per group). FIG. 12B graphically represents a blood glucose level over time in subjects following an intra-peritoneal glucose tolerance test (IPGTT). IPGTT, an evaluation of glycemic control following insulin injection, was performed by injection with 2.5 U/ml of insulin in db/db mice fed 4-MU or control chow continuously for 2 weeks. Data are representative of 2 independent experiments. *=p<0.05 for the comparison between control and 4-MUG chow. Data represent mean±SEM.

EXAMPLE 2

Delay of Onset of Diabetes

The present examples shows that compound B (Butyl-4-MUG) delays the onset of diabetes at $\frac{1}{100}^{th}$ the dose of 4-MU. This result is very surprising, particularly because 0.65% (approximately 10× less) 4-MU is only partially protective. Without wishing to be bound by theory, it is believed that 4-MU has low in vivo exposure and low bioavailability (~2-3%), because it is rapidly glucuronidated by first-pass metabolism, and the glucuronide (4-MUG) is rapidly excreted. Since a 4-MUG derivative is already a glucuronide, it escapes first-pass metabolism, giving it a large advantage in in vivo exposure.

In proof-of-principle studies, 12 candidate esters of 4-MU and 4 candidate esters of 4-MUG were generated and the conversion of these compounds into 4-MU in buffer containing bovin serum was examined. 8 that were readily converted into 4-MU were identified, and then two (ethyl-4-MUG, "Compound A;" and butyl-4-MUG ("Compound B")) that best inhibited HA synthesis in vitro were selected. Compounds A and B were individually administered to 8 week old DORmO mice. Compound B, butyl-4-MUG, delayed diabetes onset by one month when compared to Compound A. In contrast, mice fed Compound A, ethyl-4-MUG, developed diabetes at 12 weeks of age, at the same time as untreated DORmO mice. Notably, both pro-drugs were administered at $\frac{1}{100}^{th}$ of the concentration of 4-MU, suggesting that higher dosages of butyl-4-MUG may prove efficacious. These results indicate that a pro-drug strategy to increase the bioavailability of 4-MUG is feasible and pharmacologically sound.

DORmO Mice

DORmO mice were described in International Application No. PCT/US2014/050770, filed an Aug. 12, 2014 and entitled "4-Methylumbelliferone Treatment for Immune Modulation," herein incorporated by reference in its entirety.

Briefly, to determine that HA accumulates in the pancreatic islets and creates a permissive environment for autoimmune attacks during autoimmune diabetes disease progression, the DORmO double transgenic mouse model of autoimmune diabetes was used. DORmO mice predictably develop autoimmune diabetes because they are bred to have both a target antigen on their insulin producing beta-cells as well as an immune system that specifically recognizes that antigen. DORmO mice are the result of a cross between RIPmOVA mice (a strain that carries a gene specific for hen egg ovalbumin (OVA) that is only expressed on beta-cells, emulating the auto-antigen) and DO11.10 mice (a strain that carries a T-cell receptor transgene specific for OVA, emulating auto-reactive CD4+ T cells). DORmO mice spontaneously develop autoimmune insulitis starting at four weeks of age and all animals become diabetic (hyperglycemia >200 mg/dl) by 20 weeks of age (Wesley, J. D., et al., *J. Immunol.* 185, 4760-4768 (2010). DORmO mice have spontaneous autoimmunity which closely parallels the inflammatory beta-cell destruction found in humans.

Mice

All animals were bred and maintained under specific pathogen-free conditions, with free access to food and water, in the animal facilities at Stanford University Medical School (Stanford, Calif.). B6.db/db LeptR$^{-/-}$ mice were purchased from Jackson Laboratories (JAX) as well as DO11.10 transgenic mice. The DO11.10 mice were bred with BALB/c mice expressing RIPmOva (available at the Benaroya Research Institute) to generate the DORmO double-transgenic mice. In addition C57BL/6J mice were bred in house at Stanford University School of Medicine. All animal experiments and use procedures were approved by the Institutional Animal Care & Use Committee at Stanford University School of Medicine.

Mice Diabetes Monitoring

Beginning at four weeks of age, mice were weighed weekly as well as bled via the tail vein for the determination of their blood glucose level using a Contour blood glucose meter and blood glucose monitoring strips (Bayer Healthcare). When two consecutive blood glucose readings of 250 mg/dL were recorded, animals were considered diabetic. When two consecutive blood glucose readings of 300 mg/dL were recorded, animals were euthanized.

4-MU and 4-MUG Treatment

The 4-MU (Alfa Aesar) was pressed into the mouse chow by TestDiet® and irradiated before shipment. This chow formulation delivered 250 mg/mouse/day, yielding a serum drug concentration of 640.3±17.2 nmol/L in mice, as measured by HPLC-MS. 4-MUG (ChemImpex) was distributed in the drinking water of the mice at a 5% concentration which should deliver 0.325 mg/mouse/day, yielding a serum drug concentration of 357.1±72.6 ng/mL in mice, as measured by HPLC-MS. Mice were initiated on 4-MU and 4-MUG at five, eight or twelve weeks of age, unless otherwise noted, and were maintained on this diet until they were euthanized, unless otherwise noted. For analysis of Foxp3+ regulatory T cell numbers in naïve mice, mice were treated daily with 0.5 mg of 4-MU or 1.0 mg 4-MUG in 200 µl 0.08% carboxymethylcellulose in saline by intraperitoneal (i.p.) injection.

For the in vivo part the oral delivery in the drinking water was the same as for 4-MUG. The mice receive the prodrug it in their water, water bottles were changed every other day, mice had access the water ad libitum. Compounds A and B were delivered as 0.05% in water, not 5%.

While the preferred embodiment of the invention has been illustrated and described, it will be appreciated that various changes can be made therein without departing from the spirit and scope of the invention.

The invention claimed is:

1. A compound of Formula (I):

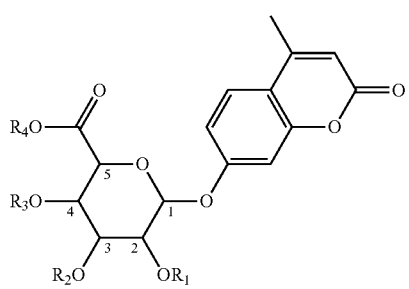

wherein
$R_1$ and $R_2$ are each independently selected from H, C(O)—$C_{1-10}$ alkyl, and C(O)—$C_{1-10}$ haloalkyl;
$R_3$ is selected from H, C(O)—$C_{1-10}$ alkyl, C(O)—$C_{1-10}$ haloalkyl, C(O)—$C_{6-10}$ aryl, and C(O)—$C_{5-10}$ heteroaryl, wherein the C(O)—$C_{1-10}$ haloalkyl, C(O)—$C_{6-10}$ aryl, and C(O)—$C_{5-10}$ heteroaryl are each optionally substituted with 1, 2, 3, or 4 substituents independently selected from halo, cyano, and nitro; and
$R_4$ is selected from $C_{2-10}$ alkyl and $C_{2-10}$ haloalkyl, or a pharmaceutically acceptable salt thereof.

2. The compound of claim 1, wherein $OR_1$ is in a down position.
3. The compound of claim 1, wherein $OR_2$ is in an up position.
4. The compound of claim 1, wherein $R_1$ and $R_2$ are each independently selected from H and C(O)—$C_{1-10}$ alkyl.
5. The compound of claim 1, wherein $R_1$ and $R_2$ are each independently selected from H, C(O)-ethyl, and C(O)-methyl.
6. The compound of claim 1, wherein $R_1$ and $R_2$ are each independently selected from H and C(O)-methyl.
7. The compound of claim 1, wherein $OR_3$ is in a down position.
8. The compound of claim 1, wherein $R_3$ is selected from H and C(O)—$C_{1-10}$ alkyl.
9. The compound of claim 1, wherein $R_3$ is selected from H, C(O)-ethyl, and C(O)-methyl.
10. The compound of claim 1, wherein $R_3$ is selected from H and C(O)-methyl.
11. The compound of claim 1, wherein $C(O)OR_4$ is in a up position.
12. The compound of claim 1, wherein $R_4$ is $C_{2-10}$ alkyl.
13. The compound of claim 1, wherein $R_4$ is selected from ethyl, propyl, and butyl.
14. The compound of claim 1, wherein $R_4$ is selected from ethyl and butyl.

15. The compound of claim 1, wherein the compound of Formula (I) is a β-glucoside.
16. A compound of claim 1, selected from

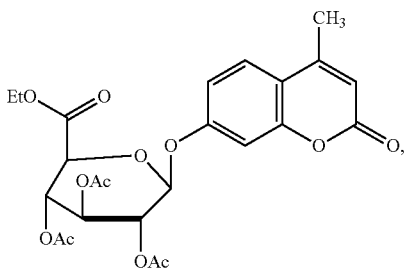

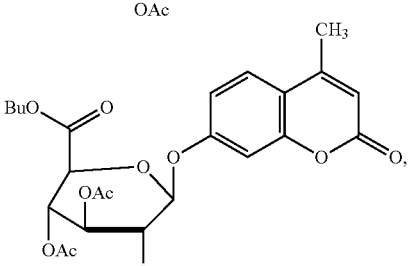

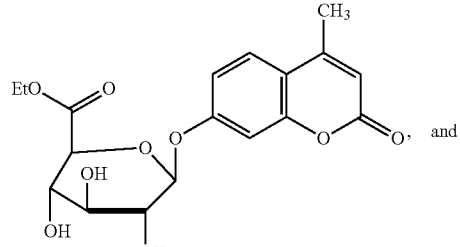

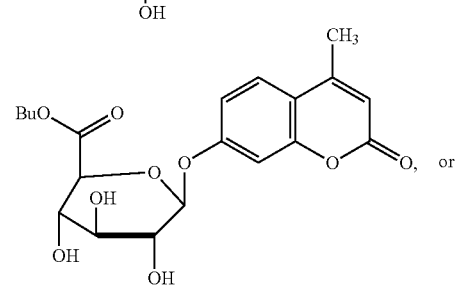

a pharmaceutically acceptable salt thereof.

17. A composition comprising a compound of claim 1, or a pharmaceutically acceptable salt thereof, and a pharmaceutically acceptable carrier.
18. A method for intracellular delivery of a compound of claim 1, comprising contacting a cell with a compound of claim 1.
19. A method of inducing a regulatory T-cell response, inhibiting hyaluronan synthesis in a subject, or increasing FoxP3+ regulatory T-cells, comprising administering to a subject a therapeutically effective amount of a compound of claim 1, or a pharmaceutically acceptable salt thereof.
20. A method of treating inflammatory, autoimmune, allergic, or atopic disease in a subject, comprising administering to the subject a therapeutically effective amount of a compound of claim 1, or a pharmaceutically acceptable salt thereof, wherein the inflammatory, autoimmune, allergic, or atopic disease is selected from the group consisting of type 1 diabetes, type 2 diabetes, multiple sclerosis, Sjögrens disease, autoimmune thyroiditis, primary sclerosing cholangitis, rheumatoid arthritis, psoriasis, colitis, lichen planus, psoriasis, eczema, and asthma.

21. A method for treating insulitis and/or reversing progression of diabetes in a subject suffering from or at risk of developing diabetes, the method comprising:
   administering to the subject a composition comprising a compound of claim 1, or a pharmaceutically acceptable salt thereof, in an amount effective to inhibit hyaluronan synthesis in the subject.

22. A method for treating multiple sclerosis and/or autoimmune demyelination in a subject suffering from or at risk of developing multiple sclerosis, the method comprising:
   administering to the subject a composition comprising a compound of claim 1, or a pharmaceutically acceptable salt thereof, in an amount effective to inhibit hyaluronan synthesis in the subject.

\* \* \* \* \*